US006596512B1

(12) United States Patent
Blakely et al.

(10) Patent No.: US 6,596,512 B1
(45) Date of Patent: Jul. 22, 2003

(54) NUCLEIC ACID ENCODING NEMATODE DOPAMINE TRANSPORTER AND THE PROTEIN ENCODED THEREBY

(75) Inventors: Randy D. Blakely, Brentwood, TN (US); Cecil M. Eppler, Langhorne, PA (US)

(73) Assignees: American Cyanamid Company, Madison, NJ (US); Vanderbilt University, Nashville, TN (US)

( * ) Notice: Subject to any disclaimer, the term of this patent is extended or adjusted under 35 U.S.C. 154(b) by 0 days.

(21) Appl. No.: 09/530,157

(22) PCT Filed: Oct. 27, 1998

(86) PCT No.: PCT/US98/22712

§ 371 (c)(1),
(2), (4) Date: Jul. 18, 2000

(87) PCT Pub. No.: WO99/21883

PCT Pub. Date: May 6, 1999

Related U.S. Application Data

(60) Provisional application No. 60/063,282, filed on Oct. 27, 1997.

(51) Int. Cl.[7] .......................... C07K 14/705; C12N 5/10; C12N 15/12; C12N 15/63; G01N 33/53
(52) U.S. Cl. ..................... 435/69.1; 435/71.1; 435/71.2; 435/320.1; 435/325; 435/471; 435/252.3; 435/254.11; 435/254.2; 435/367; 435/7.1; 435/7.2; 435/7.21; 435/6; 550/350; 536/23.5
(58) Field of Search ............................ 536/23.1, 23.5, 536/24.3, 24.31; 435/69.1, 71.1, 71.2, 471, 325, 252.3, 254.11, 367, 254.2, 7.1, 7.2, 7.21, 320.1, 6; 530/350

(56) References Cited

U.S. PATENT DOCUMENTS 5,580,775 A    12/1996    Fremeau, Jr. et al.

FOREIGN PATENT DOCUMENTS

WO    WO 93/06238    4/1993
WO    WO 99/21883    5/1999

OTHER PUBLICATIONS

Wilson et al., Nature, Vol. 368: 32–38 (1994).*
Jayanthi et al., Molecular Pharmacology, Vol. 54, 601–609, 1998.*
Adkins, et al., "Antagonist and Substrate Recognition by the Serotonin Transporter Probed by Species–Scanning Mutagenesis," *Society for Neuroscience*, Vol. 23:404–162.8 (1997).
Alwine, et al., "Detection of Specific RNAs or Specific Fragments of DNA by Fractionation in Gels and Transfer to Diazobenzyloxymethyl Paper," *Methods in Enzymology*, Vol. 68:220–242 (1979).

Apparsundaram, et al., "Molecular Cloning and Characterization of an L–Epinephrine Transporter from Sympathetic Ganglia of the Bullfrog, Rana catesbiana," *The Journal of Neuroscience*, Vol. 17(8):2691–2702 (1997).
Apparsundaram, et al. "Role of Phosphoinositol–3–Kinase in the Acute Regulation of Human Norepinephrine Transporters,"*Society for Neuroscience*, Vol. 23, 450.5 (1997).
Ausubel, et al., Current Protocols in Molecular Biology, Vol. 1 (John Wiley and Sons, 1987) (Table of Contents).
Barker, et al., "Chimeric Human and Rat Serotonin Transporters Reveal Domains Involved in Recognition of Transporter Ligands," *Molecular Pharmacology*, Vol. 46:799–807 (1994).
Barker and Blakely, "Norepinephrine and Serotonin Transporters/Molecular Targets of Antidepressant Drugs," *Psychopharmacology: The Fourth Generation of Progress*, Chapter 28:321–333 (1995).
Barker and Blakely, "Identification of a Single Amino Acid, Phenylalanine 586, That is Responsible for High Affinity Interactions of Tricyclic Antidepressants with the Human Serotonin Transporter," *Molecular Pharmacology*, Vol. 50:957–965 (1996).
Barker and Blakely, "A Conserved Aspartate in TMD I Interacts with Substrates of the Monoamine Neurotransmitter Transporters," *Society for Neuroscience*, Vol. 23:1131–450.4 (1997).
Barker and Blakely, "Structural Determination of Neurotransmitter Transport using Cross–Species Chimeras: Studies on Serotonin Transporter," *Methods in Enzymology*, Vol. 296:475–498 (1998).
Blakely, et al., "Vaccinia–T7 RNA Polymerase Expression System: Evaluation for the Expression Cloning of Plasma Membrane Transporters," *Analytical Biochemistry*, Vol. 194:302–308 (1991).
Blakely, et al., "Cloning and expression of a functional serotonin transporter from rat brain," *Letters to Nature*, Vol. 354:66–70 (1991).
Blakely, et al., "Regulation of Antidepressant–Sensitive Serotonin Transporters," *Neurotransmitter Transporters: Structure, Function, and Regulation*, Chapter 2:29–72 (1997).
Blaxter, et al., "Nematode Spliced Leaders—Ubiquity, Evolution and Utility," *International Journal for Parasitology*, Vol. 26: No. 10. pp. 1025–1033 (1996).
Blier and de Montigny, "Current advances and trends in the treatment of depression," *Elseyier Science, Ltd.*, TiPS, Vol. 15:220–226 (1994).

(List continued on next page.)

Primary Examiner—Prema Mertz
(74) Attorney, Agent, or Firm—Kilpatrick Stockton LLP; Bruce D. Gray; Kristin D. Mallatt

(57) ABSTRACT

A nematode dopamine tansporter cDNA has been cloned, sequenced, and expressed, and provides a convenient screening assay for antiparasitics, as well as psychoactive drugs.

17 Claims, 5 Drawing Sheets

Bruss, et al., "Antipeptide Antibodies Confirm the Topology of the Human Norepinephrine Transporter," *The Journal of Biological Chemistry*, Vol. 270: No. 16, Issue of Apr. 21, pp. 9197–9201 (1995).

Buck and Amara, "Chimeric dopamine—norepinephrine transproters delineate structural domains influencing selectivity for catecholamines and 1–methyl–4–phenylpyridinium," *Proc. Natl. Acad. Sci. USA*, Vol. 91:12584–12588 (1994).

Carroll, et al., "Dopamine Transporter Blockers–Structure–Activity Relationships," *Neurotransmitter Transporters: Structure, Function, and Regulation*, Chapter 9:263–295 (1997).

Cheng, et al., "Relationship between the Inhibition Constant ($K_I$) and the Concentration of Inhibitor which causes 50 per cent Inhibition ($I_{50}$) of an Enzymatic Reaction," *Biochemical Pharmacology*, Vol. 22:3099–3108 (1973).

Conrad, et al., "SLI trans–splicing specified by AU–rich synthetic RNA inserted at the 5' end of *Caenorhabditis elegans* pre–mRNA," *Cambridge Press, RNA*, Vol. 1:164–170 (1995).

Corey, et al, "A cocaine–sensitive Drosophila serotonin transporter: Cloning, expression, and electrophysiological characterization," *Proc. Natl. Acad. Sci. USA, Neurobiology*, Vol. 91:1188–1192 (1994).

Coyle and Snyder, "Catecholamine Uptake by Synaptosomes in Homogenates of Rat Brain: Stereospecificity in Different Areas," *The Journal of Pharmacology and Experimental Therapeutics*, Vol. 170, No. 2:221–231 (1969).

Davis, et al., A Manual for Genetic Engineering—Advanced Bacterial Genetics (Cold Spring Harbor Laboratory, Cold Springs, New York) (1980) (Table of Contents).

Demchyshyn, et al, "Cloning, expression, and localization of a chloride–facilitated, cocaine–sensitive serotonin transporter from Drosophila melanogaster," *Proc. Natl. Acad. Sci. USA, Pharmacology*, Vol. 91:5158–5162 (1994).

Fuller and Wong, "Serotonin Uptake and Serotonin Uptake Inhibition," *Annals New York Academy of Sciences*, Vol. 600:68–78 (1990).

Gerhardt, et al., "Molecular Cloning and Pharmacological Characterization of a Molluscan Octopamine Receptor," *Molecular Pharmacology*, Vol. 51:293–300 (1997).

Giros, et al., "Cloning and functional characterization of a cocaine–sensitive dopamine transporter," *Federation of European Biochemical Societies*, Vol. 295, No. 1, 2, 3:149–154 (1991).

Giros, et al., "Molecular characterization of the dopamine transporter," *Elsevier Science Publishers Ltd. (UK)–TiPS*, Vol. 14:43–49 (1993).

Giros, et al., "Delineation of Discrete Domains for Substrate, Cocaine, and Tricyclic Antidepressant Interactions Using Chimeric Dopamine–Norepinephrine Transporters," *The Journal of Biological Chemistry*, Vol. 269, No. 23, Issue of Jun. 10, pp. 15985–15988 (1994).

Giros, et al., "Hyperlocomotion and indifference to cocaine and amphetamine in mice lacking the dopamine transporter," *Nature*, Vol. 379:606–612 (1996).

Graham and Van Der, "A New Technique for the Assay of Infectivity of Human Adenovirus 5 DNA," *Virology*, Vol. 52:456–467 (1973).

Guastella, et al., "Cloning and Expression of a Rat Brain GABA Transporter," *Science*, Vol. 249:1303–1306 (1990).

Harlow and Lane, Using Antibodies: A Laboratory Manual, Cold Spring Harbor Laboratory Press, Cold Spring Harbor, New York (1999) (Table of Contents).

Hoffman, "Molecular Biology of Dopamine Transporters," *Dopamine Receptors and Transporters–Pharmacology, Structure, and Function*, (Edited by Hyman B. Niznik–Clarke Institute of Psychiatry–Copyright by Marcel Dekker, Inc.) Chapter 30:645–668 (1994).

Horvitz, et al., "Serotonin and Octopamine in the Nematode," *Science*, Vol. 216:1012–1014 (1982).

Huang et al., "*Caenorhabditis elegans*: Effects of 5–Hydroxytryptophan and Dopamine on Behavior and Development," *Experimental Parasitology*, Vol. 54:72–79 (1982).

Huff, et al., "Phorbol Esters Increase Dopamine Transporter Phosphorylation and Decrease Transport $V_{max}$," *Journal of Neurochemistry*, Vol. 68, No. 1:225–232 (1997).

Iversen, Role of transmitter uptake mechanisms in synaptic neurotransmission,: *Br. J. Pharmac.*, Vol. 41:571–591 (1971).

Jayanthi, et al., "The *Caenorhabditis elegans* Gene T23G5.5 Encodes an Antidepressant– and Cocaine–Sensitive Dopamine Transporter," *Molecular Pharmacology*, Vol. 54:601–609 (1998).

Jayanthi, et al., "Neurotransmitter Transporter Genes in C. Elecans," *Society for Neuroscience*, Vol. 23, 450.6 (1997).

Kawarai, et al., "Structure and organization of the gene encoding human dopamine transporter," *Gene*, 195:11–18 (1997).

Kim, et al., "Clustering of Shaker–type $K^+$ channels by interaction with a family of membrane–associated guanylate kinases," *Nature*, Vol. 378:85–88 (1995).

Kilty, et al., "Cloning and Expression of a Cocaine–Sensitive Rat Dopamine Transporter," *Science*, Vol. 254:578–580 (1991).

Kimura and Dulbecco, "Isolation and Characterization of Temperature–Sensitive Mutants of Simian Virus 40," *Virology*, Vol. 49:394–403 (1972).

Kisiel, et al., "Biogenic Amines in the Free–Living Nematode," *Experimental Aging Research*, Vol. 2:37–44 (1976).

Kitayama, et al., "Dopamine transporter site–directed mutations differentially alter substrate transport and cocaine binding," *Proc. Natl. Acad. Sci. USA–Neurobiology*, Vol. 89:7782–7785 (1992).

Kornfeld and Kornfeld, "Assembly of Asparagine–Linked Oligosaccharides," *Ann. Rev. Biochem.*, Vol. 54:631–664 (1985).

Kozak, "Compilation and analysis of sequences upstream from the translational start site in eukaryotic mRNAs," *Nucleic Acids Research*, Vol. 12, No. 2:857–872 (1984).

Kozak, "Point Mutations Define a Sequence Flanking the AUG Initiator Codon That Modulates Translation by Eukaryotic Ribosomes," *Cell*, Vol. 44:283–292 (1986).

Kravitz, "Hormonal Control of Behavior: Amines and the Biasing of Behavioral Output in Lobsters," *Science*, Vol. 241:1775–1781 (1988).

Kuhar, et al., "The dopamine hypothesis of the reinforcing properties of cocaine," *TINS*, Vol. 14, No. 7:299–302 (1991).

Melikian, et al., "Inability to N–Glycosylate the Human Norepinephrine Transporter Reduces Protein Stability, Surface Trafficking, and Transport Activity but Not Ligand Recognition," *Molecular Pharmacology*, Vol. 50:266–276 (1996).

Messing, et al., "A system for shotgun DNA sequencing," *Nucleic Acids Research,* Vol. 9, No. 2:309–321 (1981).

Mulholland, et al., "Brain Serotonergic Deficits Measured in Vivo in P–Chloroamphetamine Rats Using Novel Carbon–II Labeled Naphthyl– and Isopropenylphenyl–Tropane Transporter Ligadns," *Society for Neuroscience,* Vol. 23, 450.8 (1997).

Nirenberg, et al., "The Dopamine Transporter is Localized to Dendritic and Axonal Plasma Membranes of Nigostriatal Dopaminergic Neurons," *The Journal of Neuroscience,* Vol. 16(2):436–447 (1996).

Pacholczyk, et al., "Expression cloning of a cocaine–and antidepressant–sensitive human noradrenaliine transporter," *Nature,* Vol. 350:350–354 (1991).

Patel, et al., "Neurotransmitter Transporter Proteins–Post-translational Modifications," *Neurotransmitter Transporters–Structure, Function, and Regulation,* (Edited by Maarten E. A. Reith–College of Medicine, University of Illinois, Peoria, IL), Chapter 9:241–262 (1997).

Potter, et al., "Enhancer–dependent expression of human ? immunoglobulin genes introduced into mouse Pre–B lymphocytes by electroporation," *Proc. Natl. Acad. Sci. USA,* Vol. 81:7161–7165 (1984).

Povlock and Amara, "The Structure and Function of Norepinephrine, Dopamine, and Serotonin Transporters," *Neurotransmitter Transporters–Structure, Function, and Regulation,* (Edited by Maarten E. A. Reith–College of Medicine, University of Illinois, Peoria, IL) Chapter 1:1–28 (1997).

Ramamoorthy, et al., "Antidepressant–and cocaine–sensitive human serotonin transporter: Molecular cloning, expression, and chromosomal localization," *Proc. Natl. Acad. Sci. USA,* Vol. 90:2542–2546, (1993).

Ramamoorthy, et al., "Phosphorylation and Regulation of Antidepressant–Sensitive Serotonin Transporters," *The Journal of Biological Chemistry,* Vol. 273, No. 4:2458–2466 (1998).

Ramamoorthy, et al., 5HT–Modulated Phosphorylation of the Human Serotonin Transporter, *Society for Neuroscience,* Vol. 23, 450.7 (1997).

Rettig, et al., "Alteration of $Ca^{2+}$ Dependence of Neurotransmitter Release by Disruption of $Ca^{2+}$ Channel/Syntaxin Interaction," *The Journal of Neuroscience,* Vol. 17(17):6647–6656 (1997).

Ritz, et al., "Cocaine Receptors on Dopamine Transporters are Related to Self–Administration of Cocaine," *Science,* Vol. 237:1219–1223 (1987).

Rudnick & Clark, "From synapse to vesicle: the reuptake and storage of biogenic amine neurotransmitters," *Biochimica et Biophysica Acta,* Vol. 1144:249–263 (1993).

Sambrook, et al., Molecular Cloning—A Laboratory Manual, Second Edition (Cold Spring Harbor Laboratory Press (1989) (Table of Contents Book 1).

Sambrook, et al., Molecular Cloning—A Laboratory Manual, Second Edition (Cold Spring Harbor Laboratory Press (1989) (Table of Contents Book 2).

Sambrook, et al., Molecular Cloning—A Laboratory Manual, Second Edition (Cold Spring Harbor Laboratory Press (1989) (Table of Contents Book 3).

Sandri–Goldin et al., "High–Frequency Transfer of Cloned Herpes Simplex Virus Type 1 Sequences to Mammalian Cells by Protoplast Fusion," *Molecular and Cellular Biology,* Vol. 1, No. 8:743–752 (1981).

Sanger, et al., "DNA sequencing with chain–terminating inhibitors," *Proc. Natl. Acad. Science USA,* Vol. 74, No. 12:5463–5467 (1977).

Schafer and Kenyon, "A calcium–channel homologue required for adaptation to dopamine and serotonin in *Caenorhabditis elegans,*" *Nature,* Vol. 375:73–78 (1995).

Schafer, et al., "Genes Affecting Sensitivity to Serotonin in *Caenorhabditis elegans,*" *Genetics,* Vol. 143:1219–1230 (1996).

Shimada, et al., "Cloning and Expression of a Cocaine–Sensitive Dopamine Transporter Complementary DNA," *Science,* 254:576–577 (1991).

Soehnge, et al., "A neurotransmitter transporter encoded by the Drosophila inebriated gene," *Proc. Natl. Acad. Science USA,* Vol. 93:13262–13267 (1996).

Sompayrac and Danna, "Efficient infection of monkey cells with DNA of simian virus 40," *Proc. Natl. Acad. Science USA,* Vol. 78, No. 12:7575–7578 (1981).

Southern, "Detection of Specific Sequences Among DNA Fragments Separated by Gel Electrophoresis," *J. Mol. Biol.,* Vol. 98:503–517 (1975).

Strader, et al., "A Single Amino Acid Substitution in the β–Adrenergic Receptor Promotes Partial Agonist Activity from Antagonists," *The Journal of Biological Chemistry,* Vol. 254, No. 28, Issue of Oct. 5:16470–16477 (1989).

Strader, et al., "Allele–Specific Activation of Genetically Engineered Receptors," *The Journal of Biological Chemistry,* Vol. 266, No. 1, Issue of Jan. 5:5–8 (1991).

Sulston, et al., "Dopaminergic Neurons in the Nematode *Caenorhabditis elegans,*" *The Journal of Comparative Neurology,* Vol. 163, No. 2:215–226 (1975).

Surratt, et al., "Sodium– and chloride–dependent transporters in brain, kidney, and gut: lessons from complementary DNA cloning and structure–function studies," *Current Opinion in Nephrology and Hypertension,* Vol. 2, No. 3:744–760 (1993).

Tanaka, et al., "Epilepsy and Exacerbation of Brain Injury in Mice Lacking the Glutamate Transporter GLT–1", *Science,* Vol. 276:1699–1702 (1997).

Tashjian, Jr., "Clonal Strains of Hormone–Producing Pituitary Cells," *Methods in Enzymology,* Vol. LVIII:527–535 (1979).

Uhl, et al., "Transporter explosion: update on uptake," *Trends in Pharmacological Sciences,* Vol. 13:421–425 (1992).

Usdin, et al., "Cloning of the cocaine–sensitive bovine dopamine transporter," *Proc. Natl. Acad. Science USA,* Vol. 88:11168–11171 (1991).

Vaughan and Kuhar, "Dopamine Transporter Ligand Binding Domains," *The Journal of Biological Chemistry,* Vol. 271, No. 35, Issue of Aug. 30:21672–21680 (1996).

Vaughan, et al., "Protein Kinase C–mediated Phosphorylation and Functional Regulation of Dopamine Transporters in Striatal Synaptosomes," *The Journal of Biological Chemistry,* Vol. 272, No. 24, Issue of Jun. 13:15541–15546 (1997).

Weinshenker, et al., "Genetic and Pharmacological Analysis of Neurotransmitters Controlling Egg Laying in *C. elegans,*" *The Journal of Neuroscience,* Vol. 15, No. 10:6975–6985 (1995).

Wilson, et al., "2.2 Mb of contiguous nucleotide sequence from chromosome III of *C. elegans,*" *Nature,* Vol. 368:32–38 (1994).

\* cited by examiner

FIG. 5

SEQUENCE LISTING

<160> NUMBER OF SEQ ID NOS: 11

<210> SEQ ID NO 1
<211> LENGTH: 23
<212> TYPE: DNA
<213> ORGANISM: Artificial Sequence
<220> FEATURE:
<223> OTHER INFORMATION: Oligonucleotide PCR Probe RB436

<400> SEQUENCE: 1
taaccgcatt ctatgtggat ttc                                               23

<210> SEQ ID NO 2
<211> LENGTH: 24
<212> TYPE: DNA
<213> ORGANISM: Artificial Sequence
<220> FEATURE:
<223> OTHER INFORMATION: Oligonucleotide PCR Probe RB437

<400> SEQUENCE: 2
gttgcacaat tgatgaatga tgtg                                              24

<210> SEQ ID NO 3
<211> LENGTH: 25
<212> TYPE: DNA
<213> ORGANISM: Artificial Sequence
<220> FEATURE:
<223> OTHER INFORMATION: Oligonucleotide PCR Probe RB452

<400> SEQUENCE: 3
caaatcttca gacgatcccg acgaa                                             25

<210> SEQ ID NO 4
<211> LENGTH: 25
<212> TYPE: DNA
<213> ORGANISM: Artificial Sequence
<220> FEATURE:
<223> OTHER INFORMATION: Oligonucleotide PCR Probe RB453

<400> SEQUENCE: 4
ctaggataat gaaagtggaa gacac                                             25

<210> SEQ ID NO 5
<211> LENGTH: 31
<212> TYPE: DNA
<213> ORGANISM: Artificial Sequence
<220> FEATURE:
<223> OTHER INFORMATION: Oligonucleotide PCR Probe SL1 Primer

<400> SEQUENCE: 5
gcaggatccg gtttaattac ccaagcttga g                                      31

<210> SEQ ID NO 6
<211> LENGTH: 25
<212> TYPE: DNA
<213> ORGANISM: Artificial Sequence
<220> FEATURE:
<223> OTHER INFORMATION: Oligonucleotide PCR Probe RB515

<400> SEQUENCE: 6
agtccagctt tccagaccac tgttc                                             25

<210> SEQ ID NO 7
<211> LENGTH: 25

```
<212> TYPE: DNA
<213> ORGANISM: Artificial Sequence
<220> FEATURE:
<223> OTHER INFORMATION: Oligonucleotide PCR Probe RB516

<400> SEQUENCE: 7
ctggccgagg cacaactcca tgtag                                         25

<210> SEQ ID NO 8
<211> LENGTH: 37
<212> TYPE: DNA
<213> ORGANISM: Artificial Sequence
<220> FEATURE:
<223> OTHER INFORMATION: Oligonucleotide PCR Probe RB517

<400> SEQUENCE: 8
gcgcgcatgc tccatattcc aaattagtcg aaaagct                            37

<210> SEQ ID NO 9
<211> LENGTH: 2158
<212> TYPE: DNA
<213> ORGANISM: Caenorhabditis elegans
<220> FEATURE:
<221> NAME/KEY: CDS
<222> LOCATION: (70)..(1914)
<223> OTHER INFORMATION:

<400> SEQUENCE: 9
```

| | |
|---|---|
| gtccatattc caaattagtc gaaaagctga tcccgctacg gtttactcga atctcaacaa | 60 |

| | | |
|---|---|---|
| ttttagcc atg cag ttg gtg cct aca gac gat ccc gac gaa aaa atc ggt<br>         Met Gln Leu Val Pro Thr Asp Asp Pro Asp Glu Lys Ile Gly<br>         1             5                    10 | | 111 |
| cgg acg tct aat ggc atg caa aat gca act ctt cct att gat gga cca<br>Arg Thr Ser Asn Gly Met Gln Asn Ala Thr Leu Pro Ile Asp Gly Pro<br>15                   20                      25                 30 | | 159 |
| gtt aat aca gaa ccc aaa gat cca gca aga gaa cag tgg tct gga aag<br>Val Asn Thr Glu Pro Lys Asp Pro Ala Arg Glu Gln Trp Ser Gly Lys<br>                         35                      40                 45 | | 207 |
| ctg gac ttc ctt ctc tca gtt gtc ggg ttt gct gta gat ttg gga aat<br>Leu Asp Phe Leu Leu Ser Val Val Gly Phe Ala Val Asp Leu Gly Asn<br>         50                      55                      60 | | 255 |
| ata tgg cga ttt cca tat ctt tgc ttc aaa aat gga gga gga gta ttt<br>Ile Trp Arg Phe Pro Tyr Leu Cys Phe Lys Asn Gly Gly Gly Val Phe<br>65                   70                      75 | | 303 |
| ttg att cct tat tct ata atg gtc ctg ttg aca gga gtt cca cta ttc<br>Leu Ile Pro Tyr Ser Ile Met Val Leu Leu Thr Gly Val Pro Leu Phe<br>         80                      85                      90 | | 351 |
| tac atg gag ttg tgc ctc ggc cag tat tat aga aaa gga gca atc aca<br>Tyr Met Glu Leu Cys Leu Gly Gln Tyr Tyr Arg Lys Gly Ala Ile Thr<br>95                   100                   105                110 | | 399 |
| act tgg gga aga ata tgt ccg ttg ttc aaa gga atc gga tat tgt gtt<br>Thr Trp Gly Arg Ile Cys Pro Leu Phe Lys Gly Ile Gly Tyr Cys Val<br>                       115                   120                125 | | 447 |
| att tta acc gca ttc tat gtg gat ttc ttt tat aat gtg atc ctt gcc<br>Ile Leu Thr Ala Phe Tyr Val Asp Phe Phe Tyr Asn Val Ile Leu Ala<br>         130                    135                   140 | | 495 |
| tgg ggg ctt cat tat tta tat act tca ttc agt ttt aac ctg cca tgg<br>Trp Gly Leu His Tyr Leu Tyr Thr Ser Phe Ser Phe Asn Leu Pro Trp<br>               145                    150                   155 | | 543 |
| gca tcc tgt aac aac agt tat aac tct cct gct tgt tac gaa cca cac<br>Ala Ser Cys Asn Asn Ser Tyr Asn Ser Pro Ala Cys Tyr Glu Pro His<br>         160                    165                   170 | | 591 |

-continued

```
tgg tca gaa gac gga aca gca atg tgt cga agt gca aat caa tct gtc    639
Trp Ser Glu Asp Gly Thr Ala Met Cys Arg Ser Ala Asn Gln Ser Val
175                 180                 185                 190 tca gct gaa aag att tca gct gct gaa gaa tac ttt tat aag gga ttt    687
Ser Ala Glu Lys Ile Ser Ala Ala Glu Glu Tyr Phe Tyr Lys Gly Phe
            195                 200                 205 ctg ggg ctc cat gaa gca aat gca ccg aac tct cac gtt att cga agt    735
Leu Gly Leu His Glu Ala Asn Ala Pro Asn Ser His Val Ile Arg Ser
        210                 215                 220 gtc acc gat ctg gga aat gta cgt tgg gac att gct ctt tcc ctc ttc    783
Val Thr Asp Leu Gly Asn Val Arg Trp Asp Ile Ala Leu Ser Leu Phe
    225                 230                 235 gtt gtg tat ctc att tgc tac ttt tca atg tgg aaa gga atc cat act    831
Val Val Tyr Leu Ile Cys Tyr Phe Ser Met Trp Lys Gly Ile His Thr
240                 245                 250 tct gga aaa gtt gtc tgg ttt act gct cta ttt cca tat gtt gta ctg    879
Ser Gly Lys Val Val Trp Phe Thr Ala Leu Phe Pro Tyr Val Val Leu
255                 260                 265                 270 gga att cta ttc att cgt gga gtg act cta ccc gga tgg caa aac gga    927
Gly Ile Leu Phe Ile Arg Gly Val Thr Leu Pro Gly Trp Gln Asn Gly
            275                 280                 285 atc gaa tat tat ctt cga ccc aac ttt gaa atg ctc aag aga cca tcg    975
Ile Glu Tyr Tyr Leu Arg Pro Asn Phe Glu Met Leu Lys Arg Pro Ser
        290                 295                 300 gtc tgg caa gat gct gcc acg caa gta ttt ttc tca tta ggg cca gga   1023
Val Trp Gln Asp Ala Ala Thr Gln Val Phe Phe Ser Leu Gly Pro Gly
    305                 310                 315 ttc gga gtt ctc atg gca tac tcg tca tat aat gat ttc cat aat aat   1071
Phe Gly Val Leu Met Ala Tyr Ser Ser Tyr Asn Asp Phe His Asn Asn
320                 325                 330 gta tat gtg gat gct ctt ttc aca tca ttc atc aat tgt gca aca tca   1119
Val Tyr Val Asp Ala Leu Phe Thr Ser Phe Ile Asn Cys Ala Thr Ser
335                 340                 345                 350 ttt ctc tca ggg ttt gtg att ttc tcc gta ctc ggc tac atg tcc tgc   1167
Phe Leu Ser Gly Phe Val Ile Phe Ser Val Leu Gly Tyr Met Ser Cys
            355                 360                 365 aaa tct gga aaa cca att gaa gca gtt gct caa gaa ggc cct gga cta   1215
Lys Ser Gly Lys Pro Ile Glu Ala Val Ala Gln Glu Gly Pro Gly Leu
        370                 375                 380 gta ttt gta gtc tat cca gaa gca ctc tca aca atg cca tat gct cca   1263
Val Phe Val Val Tyr Pro Glu Ala Leu Ser Thr Met Pro Tyr Ala Pro
    385                 390                 395 ttc tgg tct gtg ctc ttt ttc tta atg ctc atg aca ctt ggc ctt gat   1311
Phe Trp Ser Val Leu Phe Phe Leu Met Leu Met Thr Leu Gly Leu Asp
400                 405                 410 tct tca ttc gga gga tct gaa gct atc atc acc ggc ctt tca gat gaa   1359
Ser Ser Phe Gly Gly Ser Glu Ala Ile Ile Thr Gly Leu Ser Asp Glu
415                 420                 425                 430 ttt cca ata ttg aaa aag aac aga gaa gtg ttc gtt ggt tgt ttg ttt   1407
Phe Pro Ile Leu Lys Lys Asn Arg Glu Val Phe Val Gly Cys Leu Phe
            435                 440                 445 gct ttt tac atg gta att gga att gct atg tgt aca gag ggt gga att   1455
Ala Phe Tyr Met Val Ile Gly Ile Ala Met Cys Thr Glu Gly Gly Ile
        450                 455                 460 cta atc atg gaa tgg ctc atc atc tat gga act aca tgg ggc tta ttg   1503
Leu Ile Met Glu Trp Leu Ile Ile Tyr Gly Thr Thr Trp Gly Leu Leu
    465                 470                 475 att gca gtg ttc tgt gaa gca atg gtc att gca tac atc tac ggt ctg   1551
Ile Ala Val Phe Cys Glu Ala Met Val Ile Ala Tyr Ile Tyr Gly Leu
480                 485                 490
```

```
cga caa ttt gtt cat gac gtc aaa gag atg atg gga ttc cgc ccg gga      1599
Arg Gln Phe Val His Asp Val Lys Glu Met Met Gly Phe Arg Pro Gly
495                 500                 505                 510 aat tat tgg aag ttt tgc tgg agc tgt gcc gca cca ttc att tta ttg      1647
Asn Tyr Trp Lys Phe Cys Trp Ser Cys Ala Ala Pro Phe Ile Leu Leu
                515                 520                 525 tcg atg atc act tcc aac ttc atc aat tat caa gcc ttg acc tac cag      1695
Ser Met Ile Thr Ser Asn Phe Ile Asn Tyr Gln Ala Leu Thr Tyr Gln
            530                 535                 540 gac tac aca tac cca acc gcg gca aac gtt ata gga att att ttt gcg      1743
Asp Tyr Thr Tyr Pro Thr Ala Ala Asn Val Ile Gly Ile Ile Phe Ala
        545                 550                 555 ctc tca ggc gcc tca ttt att cca ttg gta gga atc tac aaa ttc gtc      1791
Leu Ser Gly Ala Ser Phe Ile Pro Leu Val Gly Ile Tyr Lys Phe Val
    560                 565                 570 aat gcg agg ggg aac acg ata tct gag aaa tgg caa cga gtc aca atg      1839
Asn Ala Arg Gly Asn Thr Ile Ser Glu Lys Trp Gln Arg Val Thr Met
575                 580                 585                 590 cct tat cga aaa agg ccg aat caa aca gaa tat att cca att cca acc      1887
Pro Tyr Arg Lys Arg Pro Asn Gln Thr Glu Tyr Ile Pro Ile Pro Thr
                595                 600                 605 acg caa ccg cac tct gac ata atg cta tgaacatagg tgtcttccac            1934
Thr Gln Pro His Ser Asp Ile Met Leu
            610                 615 tttcattatc ctagtttcac tcgtttacac tttcatatta caccaccact ttccttcctt    1994
tagttctctc tgatatcctc ttctgttcct tttctctttg atcttttttt tttcatctct    2054
atttacactt ttaaatattt atcttttctc tttttctaa atttctttta caataaagtt     2114
acccgcctaa taagttctc taaaactaaa aaaaaaaaaa aaaa                      2158

<210> SEQ ID NO 10
<211> LENGTH: 615
<212> TYPE: PRT
<213> ORGANISM: Caenorhabditis elegans

<400> SEQUENCE: 10

Met Gln Leu Val Pro Thr Asp Pro Asp Glu Lys Ile Gly Arg Thr
1               5                   10                  15

Ser Asn Gly Met Gln Asn Ala Thr Leu Pro Ile Asp Gly Pro Val Asn
                20                  25                  30

Thr Glu Pro Lys Asp Pro Ala Arg Glu Gln Trp Ser Gly Lys Leu Asp
            35                  40                  45

Phe Leu Leu Ser Val Val Gly Phe Ala Val Asp Leu Gly Asn Ile Trp
        50                  55                  60

Arg Phe Pro Tyr Leu Cys Phe Lys Asn Gly Gly Val Phe Leu Ile
65                  70                  75                  80

Pro Tyr Ser Ile Met Val Leu Thr Gly Val Pro Leu Phe Tyr Met
                85                  90                  95

Glu Leu Cys Leu Gly Gln Tyr Tyr Arg Lys Gly Ala Ile Thr Thr Trp
            100                 105                 110

Gly Arg Ile Cys Pro Leu Phe Lys Gly Ile Gly Tyr Cys Val Ile Leu
        115                 120                 125

Thr Ala Phe Tyr Val Asp Phe Tyr Asn Val Ile Leu Ala Trp Gly
    130                 135                 140

Leu His Tyr Leu Tyr Thr Ser Phe Ser Phe Asn Leu Pro Trp Ala Ser
145                 150                 155                 160
```

-continued

```
Cys Asn Asn Ser Tyr Asn Ser Pro Ala Cys Tyr Glu Pro His Trp Ser
            165                 170                 175

Glu Asp Gly Thr Ala Met Cys Arg Ser Ala Asn Gln Ser Val Ser Ala
            180                 185                 190

Glu Lys Ile Ser Ala Ala Glu Glu Tyr Phe Tyr Lys Gly Phe Leu Gly
            195                 200                 205

Leu His Glu Ala Asn Ala Pro Asn Ser His Val Ile Arg Ser Val Thr
            210                 215                 220

Asp Leu Gly Asn Val Arg Trp Asp Ile Ala Leu Ser Leu Phe Val Val
225                 230                 235                 240

Tyr Leu Ile Cys Tyr Phe Ser Met Trp Lys Gly Ile His Thr Ser Gly
            245                 250                 255

Lys Val Val Trp Phe Thr Ala Leu Phe Pro Tyr Val Val Leu Gly Ile
            260                 265                 270

Leu Phe Ile Arg Gly Val Thr Leu Pro Gly Trp Gln Asn Gly Ile Glu
            275                 280                 285

Tyr Tyr Leu Arg Pro Asn Phe Glu Met Leu Lys Arg Pro Ser Val Trp
            290                 295                 300

Gln Asp Ala Ala Thr Gln Val Phe Phe Ser Leu Gly Pro Gly Phe Gly
305                 310                 315                 320

Val Leu Met Ala Tyr Ser Ser Tyr Asn Asp Phe His Asn Asn Val Tyr
            325                 330                 335

Val Asp Ala Leu Phe Thr Ser Phe Ile Asn Cys Ala Thr Ser Phe Leu
            340                 345                 350

Ser Gly Phe Val Ile Phe Ser Val Leu Gly Tyr Met Ser Cys Lys Ser
            355                 360                 365

Gly Lys Pro Ile Glu Ala Val Ala Gln Glu Gly Pro Gly Leu Val Phe
            370                 375                 380

Val Val Tyr Pro Glu Ala Leu Ser Thr Met Pro Tyr Ala Pro Phe Trp
385                 390                 395                 400

Ser Val Leu Phe Phe Leu Met Leu Met Thr Leu Gly Leu Asp Ser Ser
            405                 410                 415

Phe Gly Gly Ser Glu Ala Ile Ile Thr Gly Leu Ser Asp Glu Phe Pro
            420                 425                 430

Ile Leu Lys Lys Asn Arg Glu Val Phe Val Gly Cys Leu Phe Ala Phe
            435                 440                 445

Tyr Met Val Ile Gly Ile Ala Met Cys Thr Glu Gly Gly Ile Leu Ile
450                 455                 460

Met Glu Trp Leu Ile Ile Tyr Gly Thr Thr Trp Gly Leu Leu Ile Ala
465                 470                 475                 480

Val Phe Cys Glu Ala Met Val Ile Ala Tyr Ile Tyr Gly Leu Arg Gln
            485                 490                 495

Phe Val His Asp Val Lys Glu Met Met Gly Phe Arg Pro Gly Asn Tyr
            500                 505                 510

Trp Lys Phe Cys Trp Ser Cys Ala Ala Pro Phe Ile Leu Leu Ser Met
            515                 520                 525

Ile Thr Ser Asn Phe Ile Asn Tyr Gln Ala Leu Thr Tyr Gln Asp Tyr
            530                 535                 540

Thr Tyr Pro Thr Ala Ala Asn Val Ile Gly Ile Ile Phe Ala Leu Ser
545                 550                 555                 560

Gly Ala Ser Phe Ile Pro Leu Val Gly Ile Tyr Lys Phe Val Asn Ala
            565                 570                 575

Arg Gly Asn Thr Ile Ser Glu Lys Trp Gln Arg Val Thr Met Pro Tyr
```

```
                    580                 585                 590
Arg Lys Arg Pro Asn Gln Thr Glu Tyr Ile Pro Ile Pro Thr Thr Gln
        595                 600                 605
Pro His Ser Asp Ile Met Leu
    610                 615

<210> SEQ ID NO 11
<211> LENGTH: 596
<212> TYPE: PRT
<213> ORGANISM: Caenorhabditis elegans

<400> SEQUENCE: 11

Met Gln Asn Ala Thr Leu Pro Ile Asp Gly Pro Val Asn Thr Glu Pro
1               5                   10                  15
Lys Asp Pro Ala Arg Glu Gln Trp Ser Gly Lys Leu Asp Phe Leu Leu
            20                  25                  30
Ser Val Gly Phe Ala Val Asp Leu Gly Asn Ile Trp Arg Phe Pro
        35                  40                  45
Tyr Leu Cys Phe Lys Asn Gly Gly Val Phe Leu Ile Pro Tyr Ser
    50                  55                  60
Ile Met Val Leu Leu Thr Gly Val Pro Leu Phe Tyr Met Glu Leu Cys
65                  70                  75                  80
Leu Gly Gln Tyr Tyr Arg Lys Gly Ala Ile Thr Thr Trp Gly Arg Ile
                85                  90                  95
Cys Pro Leu Phe Lys Gly Ile Gly Tyr Cys Val Ile Leu Thr Ala Phe
            100                 105                 110
Tyr Val Asp Phe Phe Tyr Asn Val Ile Leu Ala Trp Gly Leu His Tyr
        115                 120                 125
Leu Tyr Thr Ser Phe Ser Phe Asn Leu Pro Trp Ala Ser Cys Asn Asn
    130                 135                 140
Ser Tyr Asn Ser Pro Ala Cys Tyr Glu Pro His Trp Ser Glu Asp Gly
145                 150                 155                 160
Thr Ala Met Cys Arg Ser Ala Asn Gln Ser Val Ser Ala Glu Lys Ile
                165                 170                 175
Ser Ala Ala Glu Glu Tyr Phe Tyr Lys Gly Phe Leu Gly Leu His Glu
            180                 185                 190
Ala Asn Ala Pro Asn Ser His Val Ile Arg Ser Val Thr Asp Leu Gly
        195                 200                 205
Asn Val Arg Trp Asp Ile Ala Leu Ser Leu Phe Val Tyr Leu Ile
    210                 215                 220
Cys Tyr Phe Ser Met Trp Lys Gly Ile His Thr Ser Gly Lys Val Val
225                 230                 235                 240
Trp Phe Thr Ala Leu Phe Pro Tyr Val Val Leu Gly Ile Leu Phe Ile
                245                 250                 255
Arg Gly Val Thr Leu Pro Gly Trp Gln Asn Gly Ile Glu Tyr Tyr Leu
            260                 265                 270
Arg Pro Asn Phe Glu Met Leu Lys Arg Pro Ser Val Trp Gln Asp Ala
        275                 280                 285
Ala Thr Gln Val Phe Phe Ser Leu Gly Pro Gly Phe Gly Val Leu Met
    290                 295                 300
Ala Tyr Ser Ser Tyr Asn Asp Phe His Asn Asn Val Tyr Val Asp Ala
305                 310                 315                 320
Leu Phe Thr Ser Phe Ile Asn Cys Ala Thr Ser Phe Leu Ser Gly Phe
                325                 330                 335
```

-continued

```
Val Ile Phe Ser Val Leu Gly Tyr Met Ser Cys Lys Ser Gly Lys Pro
            340                 345                 350

Ile Glu Ala Val Ala Gln Glu Gly Pro Gly Leu Val Phe Val Val Tyr
            355                 360                 365

Pro Glu Ala Leu Ser Thr Met Pro Tyr Ala Pro Phe Trp Ser Val Leu
    370                 375                 380

Phe Phe Leu Met Leu Met Thr Leu Gly Leu Asp Ser Ser Phe Gly Gly
385                 390                 395                 400

Ser Glu Ala Ile Ile Thr Gly Leu Ser Asp Glu Phe Pro Ile Leu Lys
            405                 410                 415

Lys Asn Arg Glu Val Phe Val Gly Cys Leu Phe Ala Phe Tyr Met Val
            420                 425                 430

Ile Gly Ile Ala Met Cys Thr Glu Gly Gly Ile Leu Ile Met Glu Trp
            435                 440                 445

Leu Ile Ile Tyr Gly Thr Thr Trp Gly Leu Leu Ile Ala Val Phe Cys
    450                 455                 460

Glu Ala Met Val Ile Ala Tyr Ile Tyr Gly Leu Arg Gln Phe Val His
465                 470                 475                 480

Asp Val Lys Glu Met Met Gly Phe Arg Pro Gly Asn Tyr Trp Lys Phe
            485                 490                 495

Cys Trp Ser Cys Ala Ala Pro Phe Ile Leu Leu Ser Met Ile Thr Ser
            500                 505                 510

Asn Phe Ile Asn Tyr Gln Ala Leu Thr Tyr Gln Asp Tyr Thr Tyr Pro
            515                 520                 525

Thr Ala Ala Asn Val Ile Gly Ile Ile Phe Ala Leu Ser Gly Ala Ser
    530                 535                 540

Phe Ile Pro Leu Val Gly Ile Tyr Lys Phe Val Asn Ala Arg Gly Asn
545                 550                 555                 560

Thr Ile Ser Glu Lys Trp Gln Arg Val Thr Met Pro Tyr Arg Lys Arg
            565                 570                 575

Pro Asn Gln Thr Glu Tyr Ile Pro Ile Pro Thr Thr Gln Pro His Ser
            580                 585                 590

Asp Ile Met Leu
        595
```

NUCLEIC ACID ENCODING NEMATODE DOPAMINE TRANSPORTER AND THE PROTEIN ENCODED THEREBY

This application claims priority to International Application Number PCT/US 98/22712 filed on Oct. 27, 1998 and published on May 6, 1999 as International Publication Number WO 99/21883, which claims priority to U.S. Provisional Application No. 60/063,282 filed on Oct. 27, 1997.

BACKGROUND OF THE INVENTION

The nature of neuronal signaling is substantially similar in all animals, ranging from simple invertebrates to man. Neuronal signals take the form of electrical impulses, generated by a change in electrical potential across the plasma membrane and propagated along the characteristically extended neuron. Individual neurons, however, are separated by gaps known as synapses which present a barrier to neuronal signaling in its electrical form. At the synapse, the signal takes the form of a chemical message relayed by a group of small signaling molecules known as neurotransmitters. Many different types of neurotransmitters have been identified, including dopamine (DA), norepinephrine (NE), γ-aminobutyric acid (GABA) and serotonin (5HT).

Neurotransmitters are stored in synaptic vesicles located in the presynaptic terminals of nerve cells. Activation of a neuron results in the generation of an electrical signal which travels the length of the cell as an action potential until it reaches the presynaptic terminal. The change in membrane potential in the terminal causes synaptic vesicles to fuse with the nerve cell membrane, prompting the release of neurotransmitter into the synaptic cleft. After traversing the cleft by diffusion, neurotransmitter binds to highly selective receptors on the membrane of the postsynaptic neuron. The nature of the postsynaptic response is dictated by the particular neurotransmitter. Excitatory neurotransmitters cause depolarization of the postsynaptic cell membrane, triggering an action potential that recreates the signal electrically in the postsynaptic neuron. In contrast, inhibitory neurotransmitters suppress activation of the postsynaptic neuron by inhibiting the formation of an action potential.

The extent of the signaling response is controlled by both the quantity of neurotransmitter released and the duration of its activity in the synapse. Many mechanisms ensure removal of the neurotransmitter from the synaptic cleft, including enzymatic destruction, active transport or reabsorption into the presynaptic neuron. Active transport is mediated by a class of transporter proteins, each specific to a particular type of neurotransmitter.

Drugs that alter brain function may impact synaptic signaling. Drugs such as cocaine and Prozac™, for example, alter brain activity by blocking the normal function of transporter proteins. Cocaine is a nonselective amine transporter antagonist which exerts its primary addictive effect by blocking dopamine transporter function. Prozac™ belongs to a class of compounds known as serotonin reuptake inhibitors, or SRRIs, that enhance the mood-elevating effects of 5HT by preventing its reabsorption into the presynaptic neuron. Other mood-altering drugs target different neurotransmitters, including Edronax™, which is used to treat severe depression and functions by altering NE levels.

A family of proteins specialized for transport and reputake of neurotransmitters has been identified and cloned. Known as the GABA/norepinephrine transporter (GAT1/NET) gene family, this group of proteins is characterized by identity of amino acid sequence as well as similarity of predicted topographies. Specifically, transporters contain 12 hydrophobic regions thought to form transmembrane domains.

Recently, multiple genes were identified in the nematode *C. elegans* as having significant homology to the GAT1/NET gene family. See Wilson et. al., *Nature* 368, 32 (1994). One such gene, T23G5.5, is located on chromosome 3, spanning cosmids CET23G5 and CET02C1. The inferred translation of T23G5.5 has high sequence similarity to a subgroup of the GAT1/NET family, the biogenic amine neurotransmitter transporters. This subgroup includes dopamine transporters (DATs), norepinephrine transporters (NE) and serotonin transporters (SERTs).

The profound behavioral effects of exogenous dopamine in *C. elegans*, including inhibition of locomotion [Schafer, W. R. et al. *Genetics* 143, 1219 (1996)] and egg laying [Horvitz, H. R. et al., *Science* 216, 1012 (1982)] indicate that dopamine uptake blockers are suitable as antihelmintic agents. Broader pesticidal effects of monarnine uptake blockers are suggested by flies with mutations in the gene inebriated, which encodes a homologue of the GAT1/NET family of transporters. These mutants display altered motor coordination in response to anesthetics.

Dopamine uptake blockers identified in high-throughput screens using heterologously expressed cDNAs of the present invention are suitable anti-parasitic agents. The cDNAs themselves are useful for synthesizing suitable probes in molecular diagnostics. The proteins expressed by the cDNAs of the present invention, CeDAT1 and CeDAT2, are useful antigens for generating specific antibodies.

It is therefore an object of the present invention to provide a nucleic acid sequence encoding a functional catecholamine/dopamine transporter from *C. elegans*.

It is a further object of the present invention to provide a nucleic acid sequence to make probes for the same protein in other species and related proteins.

It is a further object of the present invention to provide a protein, as well as an antibody, useful in research and molecular diagnostics.

It is a still further object of the present invention to provide a protein useful in the design of therapeutic transporter modulators for clinical treatment.

It is yet a further object of the present invention to provide a protein useful in the identification or design of antihelmintic compounds, as well as new psychoactive drugs.

SUMMARY OF THE INVENTION

These and other objects and advantages are obtained by the present invention, which relates to cDNA from the nematode *C. elegans* encoding at least two proteins, CeDAT1 and CeDAT2, with significant homology to mammalian biogenic amine neurotransmitter transport proteins is described. The sequences were not predictable from known DNA data bank sequences. CeDAT1 is a shortened form of CeDAT2, with 19 amino acids removed from the NH2 terminus of CeDAT2. The sequence of the cDNA has been employed to construct transfected cellular expression systems, which are useful as screening assays for psychoactive drugs that interact with mammalian biogenic amine neurotransmitter transport proteins.

PCeDAT2 was constructed by splicing sequences amplified with RB517 and RB516 into pCeDAT1 at an internal SphI site. Asterisks denote the position of in-frame stop codons.

Figure 2:
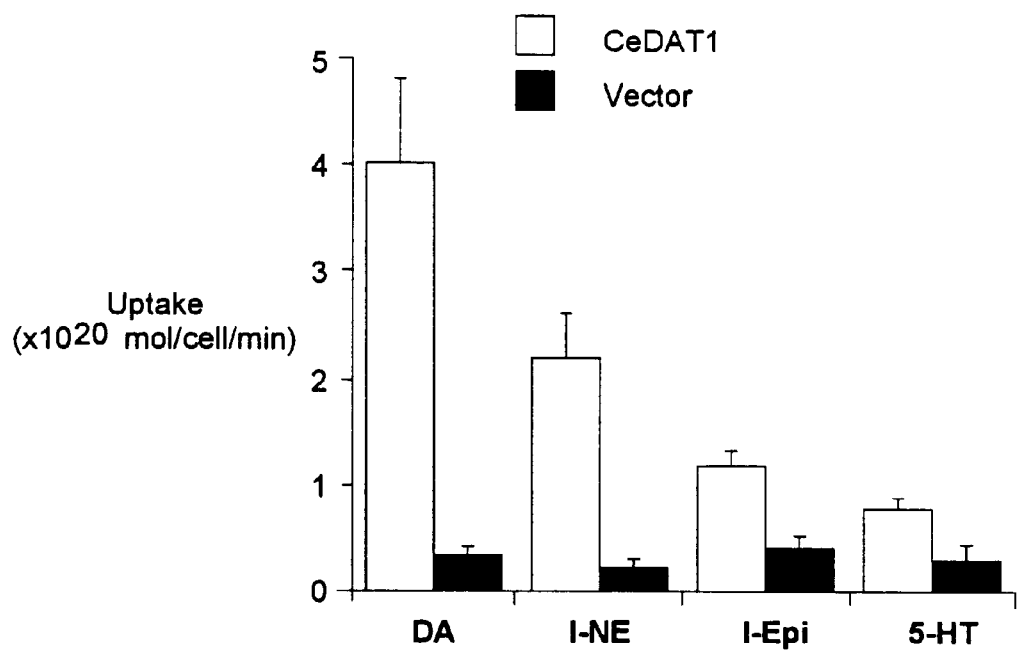
Figure 2:
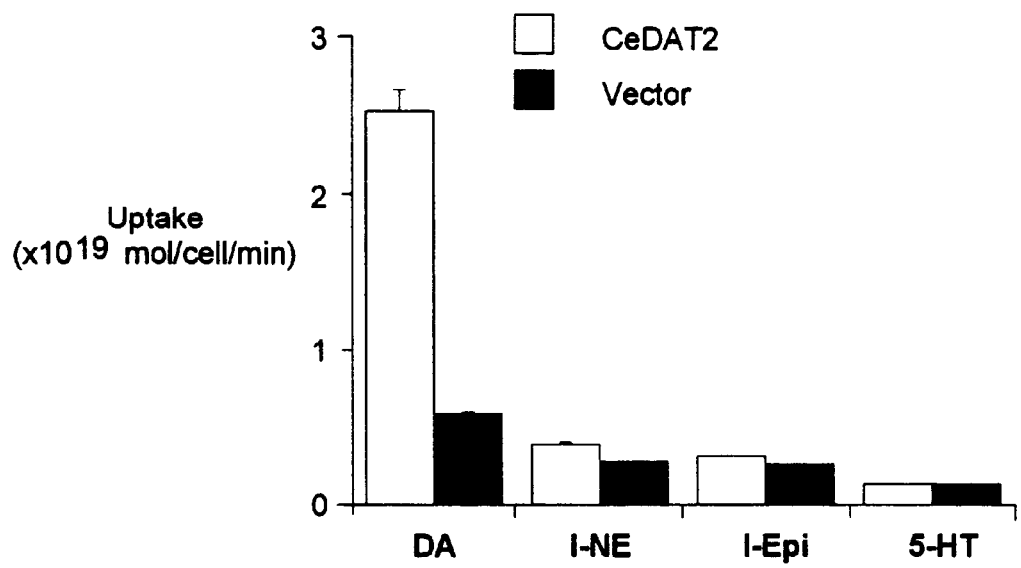

FIG. 2A sets forth the functional characterization of CeDAT1 in transiently transfected HeLa cells. Substrate selectivity assessed using either pCeDAT1 transfected cells ("CEDAT1"), or vector (pGEMTEasy) transfected cells ("VECTOR").

FIG. 2B sets forth the functional characterization of CeDAT2 in transiently transfected HeLa cells. Substrate selectivity assessed using either pCeDAT2 transfected cells ("CEDAT2"), or vector (pGEMTEasy) transfected cells ("VECTOR").

Figure 3:
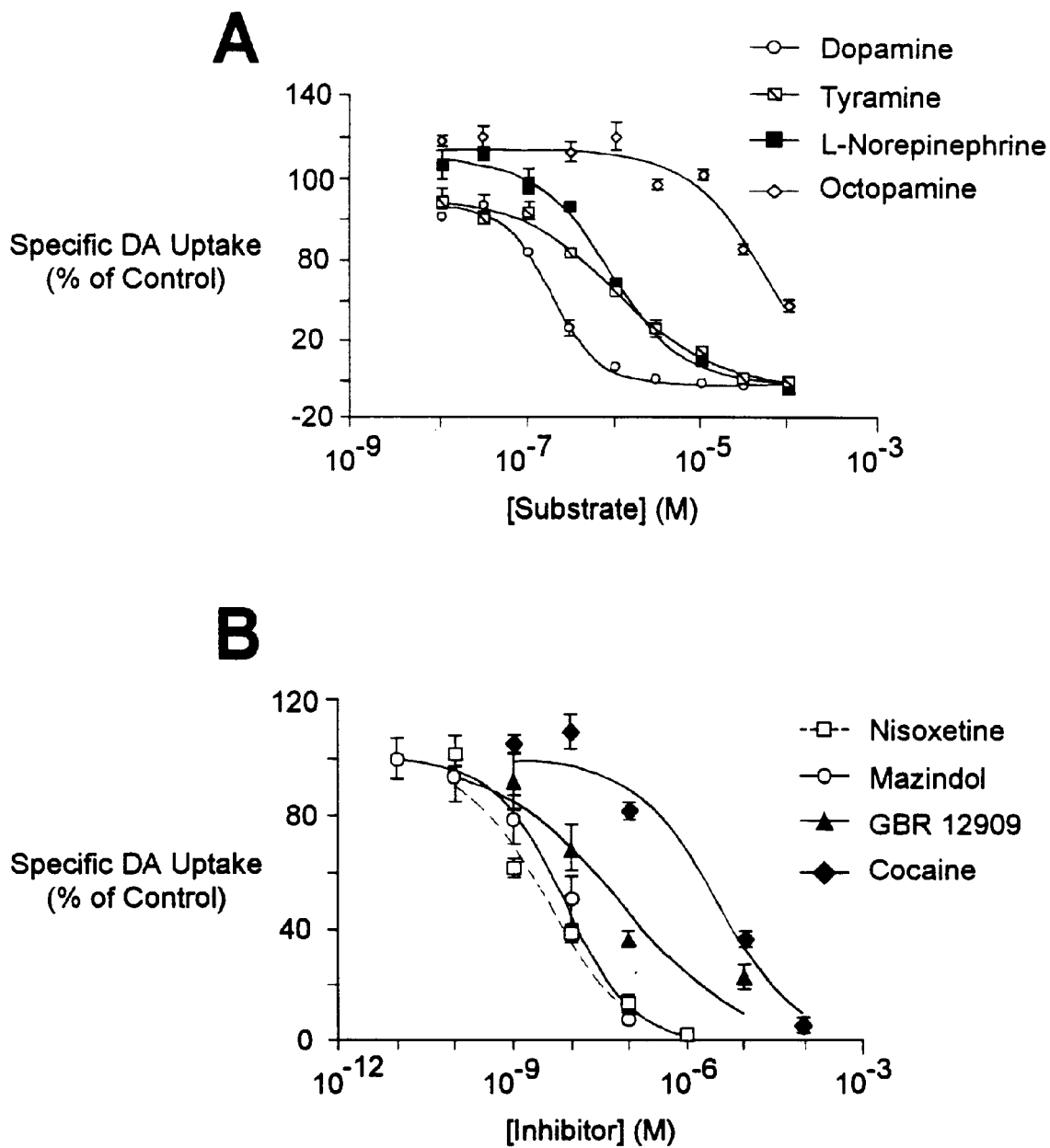

FIGS. 3A & 3B set forth inhibition profiles of [$^3$H]DA transport induced by pCeDAT1 using unlabeled substrate analogs.

Figure 4:
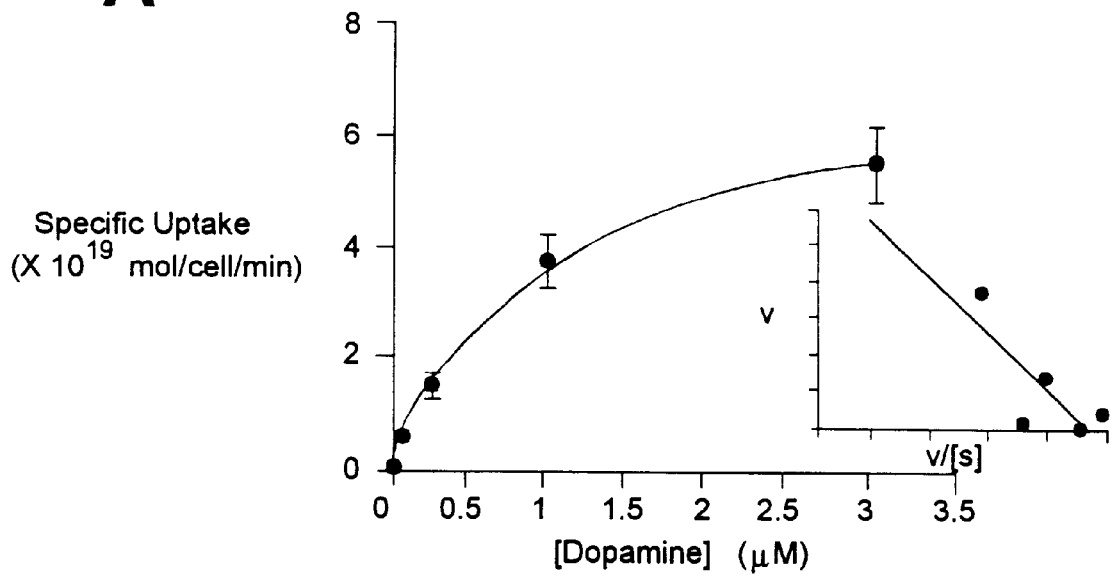
Figure 4:
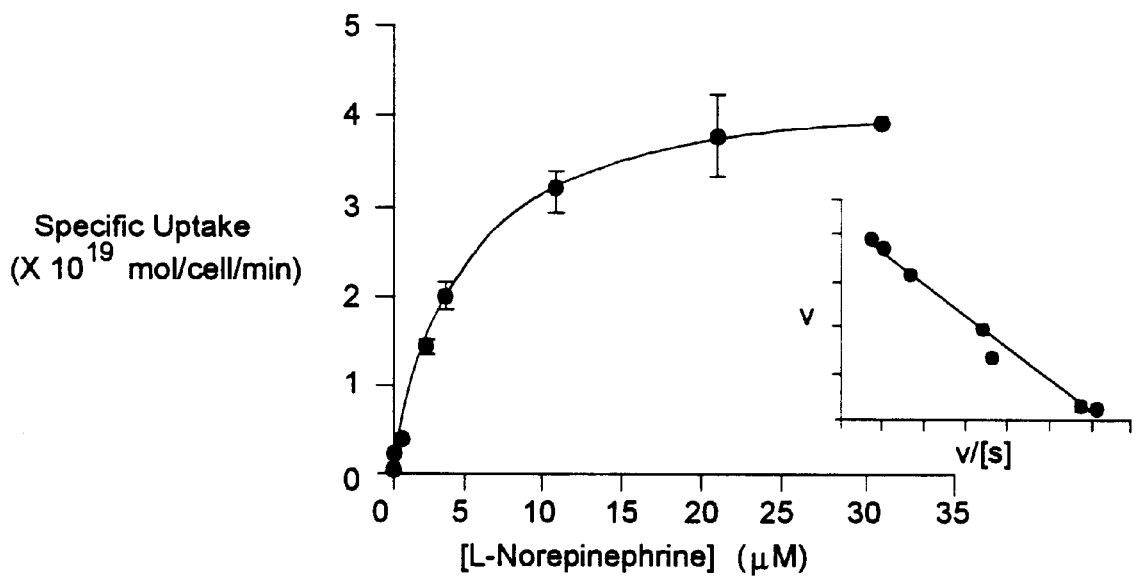

FIGS. 4A & 4B set forth saturation kinetics of catecholamine transport induced by pCeDAT1 in transfected HeLa cells. Cells were transfected with pCeDAT1 and assayed in parallel with increasing concentrations of labeled [$^3$H]DA or [$^3$H]NE. Insets represent Eadie-Hofstee replots of saturation data. $K_M$ for [$^3$H]DA was 1.2 $\mu$M and $V_{max}$ was 0.6 pmol/$10^6$ cells/min. $K_M$ for [$^3$H]NE was 4.1 $\mu$M and $V_{max}$ was 0.46 pmol/$10^6$ cells/min.

Figure 5:
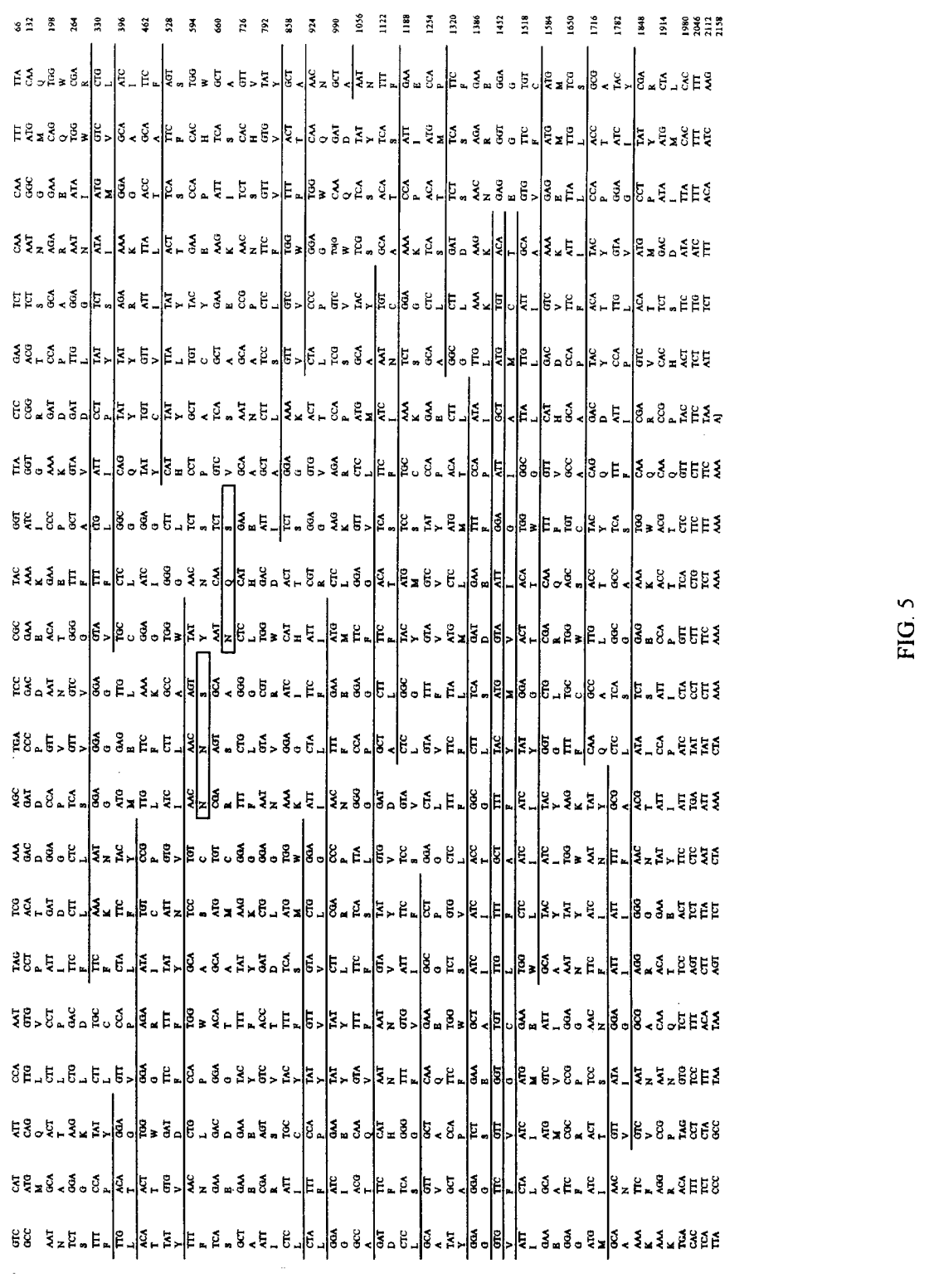

FIG. 5 sets forth CeDAT cDNA and protein sequences, including composite cDNA sequence taken from pCeDAT2 and pCET1. Highlighted sequence represents in-frame stop codons relative to the open-reading frame translated. Lines indicate an estimation of the positions of transmembrane domains from hydrophilicity analysis and comparisons with other family members. Boxed sequences reflect canonical N-glycosylation sites in the predicted extracellular domain separating TMD 3 and 4. Sequence enclosed in brackets represents that encoded by pCETλ1. Numbers reflect bp length of cDNA beginning at the SL1 primer to the poly(A) tail.

Figure 6:
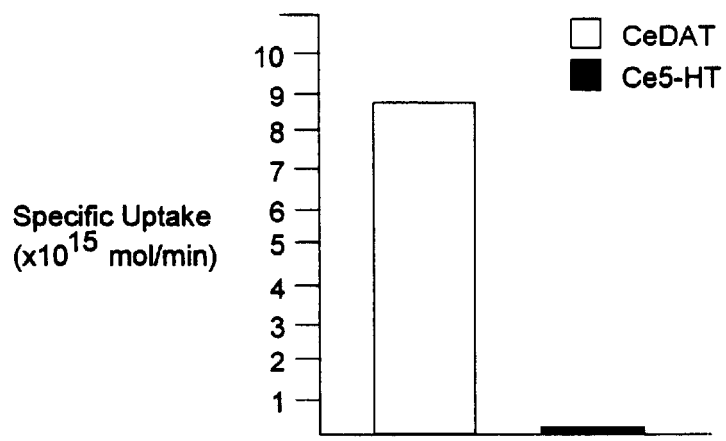

FIG. 6 sets forth the profile of [$^3$H]DA transport in GH4C1 cells stably transfected with CeDAT2 ("CeDAT2") or *C. elegans* serotonin receptor ("Ce5-HT"). Specific uptake is calculated by subtracting uptake in the presence of 1 $\mu$M imipramine from total uptake in the absence of imipramine.

DESCRIPTION OF THE SPECIFIC EMBODIMENTS OF INVENTION

The present invention relates to an isolated nucleic acid molecule encoding a nematode doparnine transporter, wherein the molecule hybridizes under standard conditions to a nucleic acid molecule complementary to the full length of SEQ ID NO:9.

One embodiment of the present invention is an isolated nucleic acid molecule encoding a nematode dopamine transporter, said transporter comprising the amino acid sequence of CeDAT2, which is SEQ ID NO:10.

Another embodiment of the present invention is an isolated nucleic acid molecule encoding a nematode dopamine transporter, said transporter comprising the amino acid sequence of CeDAT1, which is SEQ ID NO:11.

Another embodiment of the present invention is an isolated nucleic acid molecule encoding the amino acid sequence of a nematode dopamine transport protein expressed in nematodes as shown in SEQ ID NO:9, the DNA being substantially free of DNA that does not encode the amino acid sequence of SEQ ID NO:10 or a functional equivalent thereof Another embodiment of the present invention is an isolated nucleic acid molecule encoding a nematode dopamine transporter, comprising SEQ ID NO:9.

Another embodiment of the present invention is any isolated nucleic acid molecule of the present invention with a label for detection.

Another embodiment of the present invention is an expression vector comprising a nucleic acid molecule of the present invention, operatively linked to at least one control sequence compatible with a suitable host cell.

The present invention also relates to an expression system comprising a host cell transformed with the expression vector of the present invention. The host cell of the expression system can be selected from the group consisting of prokaryotes, yeast and mammalian cells. One host cell is a HeLa cell. Other host cells include MDCK cells, HEK-293 cells, and GH4C1 cells.

The present invention also relates to a process for producing a substantially purified nematode dopamine transport protein comprising the steps of:

(a) culturing a transformed host cell of the present invention, and (b) purifying the protein from the cultured host cell.

The protein prepared by this process is another embodiment of the present invention, as well as antibodies specific for the protein.

The present invention also relates to a purified dopamine transport protein comprising the sequence of amino acids as set forth in SEQ ID NO:10. The present invention also relates to a purified dopamine transport protein comprising the sequence of amino acids as set forth in SEQ ID NO:11. Antibodies specifically binding these proteins are another embodiment of the present invention.

Still another embodiment of the present invention is a purified nematode dopamine transport protein having an amino acid sequence that is substantially homologous to the sequence set forth in SEQ ID NO:10.

One method for identifying a dopamine transport antagonist, according to the present invention, comprises the steps of:

(A) providing a quantity of the expression system of the present invention;

(B) mixing said quantity with a sample of a compound to be measured;

(C) measuring inhibition of dopamine uptake.

One screening assay for dopamine transport antagonists, according to the present invention, comprises the expression system of the present invention.

Another method of the present invention identifies a dopamine transport stimulator, and comprises the steps of:

(A) providing a quantity of the expression system of the present invention;

(B) mixing said quantity with a sample of a compound to be measured;

(C) measuring enhancement of dopamine uptake.

Another screening assay of the present invention identifies dopamine transport stimulator, and comprises the expression system of the present invention.

The present invention also relates to compounds having dopamine transport antagonist activity with an $IC_{50}$ of less than or equal to about 10 $\mu$M, or compounds having dopamine transport stimulator activity with an $IC_{50}$ of less than or equal to about 10 $\mu$M, as measured by an appropriate method or screening assay of the present invention.

Still another embodiment of the present invention is a DNA probe which hybridizes to a nucleic acid molecule complementary to the full length of SEQ ID NO:9.

Another embodiment of the present invention is any DNA probe of the present invention with a label for detection.

A further embodiment of the present invention is a method for detecting the presence of a gene encoding a dopamine transporter from an organism suspected of containing the gene comprising the steps of contacting a DNA probe of the present invention with a DNA from the organism under hybridizing conditions and detecting the presence of the hybridized probe.

| ABBREVIATIONS AND DEFINITIONS | |
|---|---|
| DA | Dopamine |
| DAT | DA transporter |
| GABA | γ-Aminobutyric acid |
| 5HT | Serotonin |
| NE | Norepinephrine |
| NET | NE transporter |
| pCeDAT1 | Vector having nucleotide sequence for C. elegans DA transporter 1, which is SEQ ID NO: 9, but codes for the CeDAT1 protein with SEQ ID NO: 11 |
| pCeDAT2 | Vector having nucleotide sequence for C. elegans DA transporter 2, which is SEQ ID NO: 9, but codes for the CeDAT2 protein with SEQ ID NO: 10 |

Library Screening

Conventional library screening in combination with RT-PCR was used to identity the complete cDNA, known as CEDAT, encoding the transport protein. Results obtained by conventional screening suggested that the available cDNA library was poorly represented in T23G5.5 cDNAs with complete 5' ends and that the coding region predicted in the scientific literature for the 3' end of the T23G5.5 transcript was incorrect. RT-PCR was then used to identify the complete cDNA, as generated by an alternative splicing pattern. Transient expression of the complete cDNA in HeLa cells conferred high affinity [$^3$H] dopamine transport ($K_m$=1.2 $\mu$M). Dopamine was also the most potent competitor of [$^3$H] dopamine transport ($K_I$=146 nM). [$^3$H] DA transport was also sensitive to inhibition by tyramine ($K_I$=827 mM) and L-NE ($K_I$=1180). [$^3$H]DA transport was sensitive to inhibition by cocaine ($K_I$=3.5 $\mu$M), comparable to cloned mammalian dopamine transporters. Uptake was also very sensitive to other known mammalian transporter antagonists, including nisoxetine ($K_I$=3 nM), GBR12909 ($K_I$=70 NM) and mazindol ($K_I$=8 nM). The cloned cDNA predicts a 597 amino acid protein with 12 hydrophobic regions, thought to represent transmembrane domains. This inferred protein exhibits 37–47% amino acid sequence identity with mammalian biologic amine neurotransmitter transporters. These findings support the characterization of CEDAT as a functional catacholamine transport protein specialized for dopamine transport in the nematode *C. elegans*. This cDNA is the first of its type cloned from a nematode and is different from the cDNA predicted in scientific literature.

The cDNA is useful in a variety of contexts, many involving technqiues well known to those skilled in the art. The nucleic acid sequence can be incorporated into a host cell to generate large quantities of the transport protein for research or other purposes according to techniques well known in the art. The nucleic acid and protein can be used as probes for the same protein in other species and related proteins. Furthermore, the protein can be used to make antibodies useful in research and molecular diagnostics. The protein can also be used to design functional and structural analogs for use in research and clinical settings. The protein is useful for the identification and design of transporter modulators with clinical applications. The protein is specifically useful in the identification and design of compounds with antihelmintic, endectocidal, or psychoactive activity.

Isolation of cDNA clone for T23G5.5

Conventional library screening and RT-PCR were used to isolate a full-length cDNA clone of the hypothetical transporter gene T23G5.5. Oligonucleotide probes matching nucleotide sequences reported in cosmid CET235 [Wilson, R. et al., *Nature* 368, 32 (1994)] were created by procedures generally known to those skilled in the art. Specifically, sequences derived from hypothetical exons 2 (RB436)(SEQ ID NO:1) and 7 (RB437)(SEQ ID NO:2) were synthesized.

These oligonucleotides were used as probes to screen an oligo(dT) primed cDNA library using conventional plaque hybridization techniques that are generally known to those skilled in the art. Specifically, the probes were hybridized to plaques on Magna nylon filters.

Positive plaques were cored from master plates, and rescreened until single plaques were identified. Insert size was estimated by PCR according to a procedure generally familiar to those skilled in the art. Specifically, insert size was estimated on 0.4 $\mu$l of boiled phage stock using T3 and T7 sequencing primers (45° 1 min, 72° 3 min, 30 cycles). Inserts were excised by in vivo plasmid rescue, and sequenced according to techniques generally familiar to those skilled in the art. Specifically, inserts were sequenced with vector and internal primers, using fluorescent dye terminators.

Screening produced multiple positive plaques for probe RB437 (exon 7) but no positive isolates for probe RB436 (exon 2). PCR yielded an insert estimate of 1.1 kb for the largest insert. These results suggested that the cDNA library contained few T23G5.5 cDNA's with complete 5' ends. Sequencing confirmed the identity of these sequences as T23G5.5, with the 5' end beginning in exon 6. The 3' end of the cDNA was found to match the genomic sequence of cosmid CET02C1. However, sequence data revealed a pattern of 3' exon usage and translation termination which suggested that the GenBank hypothetical exon splicing pattern predicted for the 3' end of the T23G5.5 transcript was incorrect. Specifically, exon 11 was found to splice at base pair (bp) 26895 to exon 12 at bp 465 using canonical gt/ag donor and acceptor sites rather than at base 301, creating a new C-terminus.

This situation gives the inferred protein a longer COOH terminus (FIG. 5), following the amino acid sequence "RGNTISE" with an unpredicted set of 32 additional amino acids, and including three residues that are well conserved in catecholamine transporters from worm to man (R587, Y592, P596). Such strict conservation of these three amino acids in the otherwise highly divergent COOH terminus suggests they may serve to stabilize secondary structure of this domain that is required for recognition by physically associated accessory proteins or by regulatory protein kinases. The new stop codon is followed in the cDNA (and genomic sequence) by 227 bp of 3' noncoding sequence including a canonical polyadenylation signal (AATAAA), located 19 bp upstream of a nongenomic poly(A) tail, suggesting that the polyadenylated 3' end of the CEDAT transcript has been reached.

RT-PCR of *C. elegans* RNA

RT-PCR was used to establish a complete ORF required for expression in transfected cells. Total *C. elegans* RNA was prepared and was quality checked by 6% formaldehyde-agarose gel analysis. RT-PCR was conducted with random priming of cDNA using oligonucleotides matching genomic sequences. The sense primer (RB452) (SEQ ID NO:3) is located 5' and upstream of the predicted initiator methionine. The antisense primer (RB453) (SEQ ID NO:4) is located distal to the stop codon, and was synthesized to allow full amplification of the newly predicted ORF. See FIG. 1.

The oligonucleotide primers amplified a 1.9 kb PCR product, which appeared on ethidium stained agarose gels. The product was gel purified and ligated into vector. Multiple clones bearing the DNA insert were isolated and sequenced as decried above. Missense mutations due to PCR were corrected using nonmutated segments of subclones and by site-directed mutagenesis to establish the final expression construct, the plasmid pCEDAT1.

Figure 1:
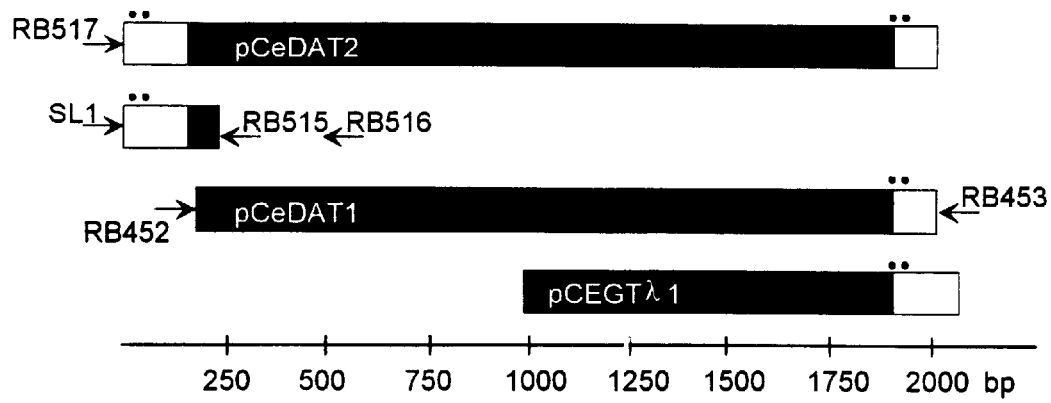
FIG. 1 schematically diagrams CeDAT cDNAs and related primers. RB452, 453, 517, and SL1 are PCR primers used to identify partial CeDAT cDNAs in *C. elegans*.

Although this cDNA for CeDAT1 induced full transport expression in transfected cells, no in-frame stop codons lay between the 5' PCR primer used to create pCeDAT1 and the predicted initiator methionine, and thus further amplifications were needed to establish the transporter's true 5' end and validate the most likely initiation site for translation. Turning again to RT-PCR, a sense primer was used complementary to the SL1 leader RNA that is transspliced to the 5' end of the majority of *C. elegans* mRNAs, and nested antisense primers downstream of the 5' end of CeDAT1 (FIG. 1). The fragment amplified using the SL1 strategy identified a new exon in the TG235.5 gene from bp 23763 to bp 23850 in cosmic CET23G5. Canonical gt/ag splice junctions splice this new first exon into exon 2 at bp 24227 (377 bp intron) just upstrean of the original, mispredicted initiator methionine. The new exon adds an additional 19 amino acids to the transporter's $NH_2$ terminus in frame with the sequence originating at the previous CeDAT1 starting methionine (FIG. 5). This sequence was transferred to pCeDAT1 to create pCeDAT2. Two in-frame stop codons precede the new start codon (GCCATGC) of pCeDAT2 and the new start codon reasonably conforms to the Kozak consensus sequence ((A/G)CCATG(G)) for translation initiation. However, translation could begin under some circumstances at Met 20, which also has a good consensus sequence (GGC<u>ATG</u>C) and pCeDAT1 expresses in transfected cells. No evidence was found in 5' RT-PCR reactions for alternative splicing of mRNA encoding the transporter's NH2 terminus. The composite sequence of the predicted CeDAT mRNA drawn from RT-PCR and phage isolates and the inferred translation of CeDAT protein is provided in FIG. 5.

Nucleotide and Inferred Amino Acid Sequence of T23G5.5

The composite sequence from the cDNA library screening and RT-PCR isolation of cDNAs is shown in the sequence listing as SEQ ID NO:10. The cDNA sequence predicts a 615 amino acid polypeptide having twelve regions of significant hydrophobicity suitable for formation of transmembrane domains (TMDs) like other members of the GAT1/NET gene family.

Two canonical sites for N-linked glycosylation are present in the large hydrophilic loop between TMDs 3 and 4. Additional N-glycosylation sites are evident in the transporters $NH_2$ (N22) and COOH (N597) termini, although direct evidence suggests analogous regions of mammalian transporter homologs are intracellular. The COOH terminal motif is preceded by a proline residue (P596) that typically renders the Asn inaccessible by the glycosylation machinery. The $NH_2$ and COOH termini possess a number of Ser and Thr residues that may be targets for regulatory phosphorylation, with two PKC sites (Ser 45, Ser 582) and one casein kinase II site (Thr 580) among these. A PKC site (Ser 255) also lies in a putative intracellular loop between TMDs 4 and 5 within a span of residues found in all catecholamine transporters. Similarly a casein kinase II site between TMDs 6 and 7 lies in a highly conserved stretch of sequence.

A comparison of the inferred amino acid sequence with those of other GAT1/NET family members demonstrates highest similarity to mammalian catecholamine transporters, about 47% amino acid identity with human, mouse and bovine NETs.

Expression of CEDAT in HeLa Cells Confers High Affinity Uptake

In the present invention, the CEDAT cDNA was transiently expressed in HeLa cells by a vaccinia-T7 virus expression system, according to Blakely, R. D. et al., *Anal. Biochem.* 194, 302 (1991). Radiolabeled DA, NE, Epi, and 5HT, each at 50 nm, was tested since CeDAT bears the greatest sequence identity with mammalian amine transporters in the GT1/NET gene family. Using pCeDAT1 which presumably initiates at the originally predicted Met 20, transfected HeLa cells were found to transport DA to a greater extent (~2 fold) than NE, with little or no transport of Epi and 5HT. See FIG. 2A. Similar results were obtained with pCeDAT2 (FIG. 2B), for which there were overall higher expression levels, but the maintained preference for DA over NE, and Epi and 5HT remained transported only at very low levels. The increased DA transport activity of pCEDAT2 vs pCEDAT2 may reflect a more efficient use of the translation initiation site present in pCEDAT2.

Competitive inhibition at the active/binding site by related analogs was next carried out. Aliquots of [$^3$H]DA and unlabeled competitors were incubated with the HeLa expression system to explore relative potencies of substrate analogs and antagonists in competing for catecholamine transport. See FIGS. 3A and 3B. For pCEDAT1, it was found that DA ($K_I$=146 nM) is almost a 10 fold more potent inhibitor of transport than L-NE ($K_I$=1180 nM), consistent with their relative $K_M$ values. Tyramine ($K_I$=827 nM) and octopamine ($K_I$=67~M) were also less potent than DA. Octopamine, a suspected neurotransmitter in invertebrates including *C. elegans*, showed low potency against CeDAT, indicating the carrier coded by CeDAT is unlikely to be involved in its clearance in vivo. D-amphetamine competed for DA transport at micromolar concentrations ($K_I$=3.3 $\mu$M) and was more potent than the L-isomer ($K_I$=13 $\mu$M), a typical selectivity associated with the mammalian L-NE transporter.

In separate experiments, the sensitivity of pCeDAT1 induced [$^3$H]DA transport to conventional amine transport antagonists was assessed. Nanomolar concentrations of the mammalian NET-selective antagonist nisoxetine ($K_I$=3 nM), the catecholamine transporter-selective antagonist mazindol ($K_I$=8 nM) and the DAT-selective antagonist GBR12909 ($K_I$=70 nM) blocked CeDAT activity. Transport could also be blocked by the nonselective amine transporter antagonist cocaine ($K_I$=3.5 $\mu$M), a potency also observed with heterologously expressed DATs.

CeDAT has a unique profile of inhibitor sensitivity, sharing pharmacologic properties with both mammalian NETs and DATs. No differences in the pharmacologic properties of pCEDAT1 versus pCEDAT2 have been found, except that CeDAT appears to drive higher levels of expression in transfected cells. CeDAT1 and CeDAT2 are each useful for a variety of screening assays, including assays for compounds having anthelmintic or psychoactive indications.

Saturation Kinetics

The true substrate for CeDAT can be inferred from the relative maximal capacities to transport different substrates. Mammalian NETs exhibit higher $V_{max}$ values for NE versus DA whereas the reverse is true for mammalian DATs. Similarly, the frog Epi transporter transports substrates with a maximal rank order velocity of Epi>NE>>DA. However, all three carriers exhibit greatest inhibitory potency for DA, suggesting that $K_I$ or $K_M$ values may be less informative than $V_{MAX}$ rank order as to the identity of native substrates.

Accordingly, saturation kinetics on pCeDAT1 transfected cells were carried out. The relative capacities of NE and DA for transport were tested, these two substrates exhibiting the greatest transport activity at low substrate concentrations. The substrate DA was found to exhibit a lower substrate $K_M$ and a higher transport $V_{MAX}$ than NE, indicating that in *C. elegans*, DA is likely to be the preferred substrate. See FIGS. 4A and 4B. There are 8 DA synthesizing neurons in *C. elegans* hermaphrodites.

These results validate the CEDAT cDNA as a functional catecholamine transporter specialized for the transport of dopamine.

Expression of CEDAT in GH4C1 Cells

CeDAT2 cDNA was also expressed in GH4C1 cells, subcloned from the GH3 cell line (ATCC No. CCL-82.1, 82.2) according to A. Tashjam Jr., *Methods in Enzymology* 58, 527 (1979). The CeDAT2 clone used to transfect HeLa cells was excised from the pGEM-T easy vector and then ligated into a vector providing superior expression stability. Specifically, CeDAT2 was excised from pGEM-T using ApaI and NotI, purified by agarose gel electrophoresis, and litigated into pcDNA3.1(−). GH4C1 cells were then transfected with the pcDNA3.1/CeDAT construct, with GH4C1 cells transfected with *C. elegans* serotonin receptor (CH4C1/Ce5-HT) serving as a control. Transfected GH4C1 cells were found to transport radiolabeled DA.

The sequence described herein is useful in a variety of contexts. The nucleic acid sequence is useful as a probe, for example, for similar or related proteins in other species. For use as a probe, the sequence is labeled with a radioisotope or other tagging system, and is incubated with immobilized denatured DNA under conditions well-known to those skilled in the art. T. Maniatis, *Molecular Cloning: A Laboratory Manual* (2nd ed. 1989). Hybridization between the probe and the source DNA is then measured using an assay appropriate to the label (e.g., autoradiography). The use of the present invention as a probe aids the phylogenetic study of transporter biology, which permits evaluation across species variants of sites responsible for substrate specificity and antagonist recognition.

The nucleic acid sequence of the present invention is also useful for cloning purposes, whereby large quantities of the dopamine transporter molecule can be generated. A variety of methods and procedures for cloning are familiar to those skilled in the art, as discussed above. T. Maniatis, *Molecular Cloning: A Laboratory Manual* (2nd ed. 1989). The availability of large quantities of dopamine transporter protein is particularly useful in the identification and design of transporter directed-pharmaceutics, including therapeutic transporter modulators and antihelmintic compounds.

Expressed protein can also be used to generate both polygonal and monoclonal antibodies. Ed Harlowe and David Lane, *Antibodies: A Laboratory Manual* (1988). In monoclonal antibody technology, immortalized tumor cells are fused with antibody producing cells to form a hybridoma capable of continually producing large quantities of specific antibody of one amino acid sequence. Both polyclonal and monoclonal antibodies are useful in research and clinical settings according to methods well known to those skilled in the art. In particular, monoclonal antibodies are useful in detection and treatment methodologies.

One principal use for the sequences of the present invention is for screening assays for agonists or antagonists of dopanine and its transporters. [Uhl, et al., *Trends in Pharmacological Sciences* 13, 421 (1992)]. Assays to screen large numbers of candidate compounds, including automated assays, are readily set up using the transfected cell system set forth in the present invention, including HeLa cells transfected with vectors for CeDAT1 or CeDAT2. Conversely, the transfected cell systems can be useful as counterscreens, as the case may be.

Protein can be expressed from cDNA using standard techniques for expression in vitro in cell free translation systems, in bacteria, yeast, and animal cells, including, insect, amphibian, avian, and mammalian cells, as well as genetically engineered, or transgenic animals. The techniques are known to those skilled in the art. Reagents, including expression vectors and cell lines, for use in these methods, are commercially available from sources such as Promega and Stratagene.

It is understood that specific cDNA sequences can be modified by those skilled in the art, for example, by labeling, fusion with regulatory sequences, insertion into expression vectors, site-directed mutagenesis and substitution or deletion of nucleotides encoding specific amino/acids, without departing from the scope of the nucleotide and amino acid sequences of the present invention, and the methods for their use.

The theories and standard procedures for molecular cloning are described in *Molecular Cloning*, edited by T. Maniatis, et al. (2nd ed. 1989) and are generally known to those skilled in the art. Procedures include preparation of DNA and RNA, preparation of cloning vectors, ligation, transformation of competent cells, selection and screening by in situ filter hybridization, as described by David, et al., *Advanced Bacterial Genetics* (Cold Spring Harbor Laboratory, Cold Spring, N.Y.). In addition, techniques for separation of DNA by gel electrophoresis, mapping of restriction enzyme cleavage sites, and modification of DNA fragments by modifying enzymes are used. Most restriction enzymes, vectors, and reagents can be obtained from commercial companies. Common vectors and *E. coli* strains are used, for example, pBR322, pUC series, lambda-WES, M13mp, DH5, LE392, JM109 and HB101.

Chain termination methods are used for nucleotide sequence determination to confirm the DNA constructs at the splicing sites, as reported by Sanger, et al. *Proc. Natl. Acad. Sci. USA* 74, 5463 (1977). Many commercial suppliers provide both reagent kits and detailed protocols. Since most nucleotide sequences are known for the vectors, promoters and genes to be used, oligonucleotides of defined sequences are used as primers in sequencing experiments. These are typically 15 to 20 nucleotides long and very convenient for sequencing specific regions of interest, using the techniques of Messing, et al. *Nucleic Acid Res.* 9, 309 (1981). Either single-stranded or double-stranded DNA can be sequenced with this technique.

Oliogonucleotides to be used in DNA sequencing and the polymerase chain reaction are synthesized by an automated DNA synthesizer. This service can be obtained from commercial sources, such as Genetic Designs, Inc., Houston, Tex. The oligonucleotides greater than 30 nucleotides are then subjected to polyacrylamide gel electrophoresis to assess purity.

DNAs are transfected into cells by one of several standard published procedures to form stable transformants, including, for example, calcium phosphate precipitation, DEAE-Dextran, electroporation, and protoplast fusion. Some of these methods are described below.

In calcium phosphate precipitation, DNAs are coprecipitated with calcium phosphate, according to the method of Graham and VanDer in *Virology* 52, 456 (1973), before transfer into cells. A quantity of 40–50 µg of DNA with salmon sperm or calf thymus DNA as carrier is used for $0.5 \times 10^6$ cells plated on a 100 mm dish. DNA is mixed with 0.5 ml of 2×Hepes solution (280 mM NaCl, 50 mM Hepes and 1.5 mM $Na_2HPO_4$, pH 7.0) to which an equal volume of 2×Ca $Cl_2$ (250 mM $CaCl_2$ and 10 mM Hepes, pH 7.0) is added. A white granular precipitate appearing after 30–40 minutes is distributed dropwise evenly on the cells and allowed to sit for 4–16 hours at 37° C. The medium is removed and the cells are shocked with 15% glycerol, the cells are fed with DMEM containing 10% fetal bovine serum and left in the incubator.

DNA can also be transferred using the DEAE-Dextran method of Kimura, et al. *Virology* 49, 394 (1972) and Sompayrac, et al., *Proc. Natl. Acad. Sci. USA* 78, 7575 (1981); the electroporation method of Potter, *Proc. Natl. Acad. Sci. USA* 81, 7161 (1984), and the protoplast fusion method of Sandri-Goddin, et al. *Molec. Cell Biol.*1,743 (1981). Another transfection method uses vaccina virus and vector encapsulated with liposomes, according to Blakely, R. D. et al., *Anal. Biochem.* 194, 302 (1991).

Standard hybridization conditions, according to the methods of the present invention, will vary with the size of the probe, the background, the concentration of the nucleic acid reagents, as well as the type of hybridization, e.g., in situ, Southern blot, or hybrization of DNA-RNA hybrids. One preferred set of standard hybridization conditions involves a blot prehybridized at 42° C. in 50% formamide, 5 times SSPE (SSPE is 150 nM NaCl, 10 mM Na $H_2PO_4$ [pH 7.4], 1 mM EDTA [pH 8.0]), 5 times Denhardt's solution (Denhardt's solution is 20 mg Ficoll, 20 mg polyvinylpyrrolidone, and 20 mg BSA per 100 ml water), 10% dextran sulphate, 1% SDS, 100 µg/ml salmon sperm DNA for 2 hours. $^{32}P$-labeled cDNA probe was added, and hybridization continued for 14 hours. The blot was rinsed with two 20 minute washes in 2 times SSPE, 0.1% SDS (22° C.), followed by a 1 hour rinse at 65° C. in 0.1 times SSPE, 0.1% SDS, and then exposed to autoradiographic film with an intensifying screen for 5 days. For additional details, see U.S. Pat. No. 5,580,775, herein incorporated by reference for these purposes. Se also Southern, E. M.,*J. Mol. Biol.* 98, 503 (1975): Alwine, J. C. et al., *Meth. Enzymol.* 68, 220 (1979).

Protein samples are prepared for Western blot analysis by lysing cells and separating proteins by SDS-PAGE. The proteins are transferred to nitrocellulose by electroblotting as described by Ausubek, et al., *Current Protocols in Molecular Biology* (John Wiley and Sons, 1987). After blocking the filter with instant nonfat dry milk (1 g in 100 ml PBS), primary antibody is added to the filter and incubated for 1 h at room temperature. The filter is washed thoroughly with phosphate buffered saline (PBS) and incubated with horseradish peroxidase (HRPO)-antibody conjugate for 1 hour at room temperature. The filter is again washed thoroughly with PBS and the antigen bands are identified by adding diaminobenzidine (DAB).

Enzyme assays, protein purification, and other classical biochemical methods are employed. DNA and RNA are analyzed by Southern blotting and Northern blotting techniques. Typically, the samples to be analyzed are size fractionated by gel electrophoresis. The gel samples, DNA or RNA, are then transferred to nitrocellulose or nylon membranes by blotting techniques. The blots, which are replicas of sample patterns in the gels, are hybridized with probes in Southern and Northen analysis. Specific bands of interest can then be visualized by detection systems such as autoradiography.

EXAMPLE 1 cDNA Library Screening: An oligo(dT) primed cDNA library in lamdazap (Stratagene) was screened by conventional plaque hybridization, according to Sambrook, J., et al., *Molecular Cloning* Cold Spring Harbor (1989), using oligonucleotides matching DNA sequences reported in COSMID CET23G5 [Wilson, R. et al., *Nature* 368, 32 (1994)] associated with a hypothetical transporter gene (T23G5.5). Oligonucleotide RB436 (sense, 5'-TAACCGCATTCTATGTGGATTTC-3', exon 2, SEQ ID NO. 1) and RB437 (antisense, 5'GTTGCACAATT-GATGAATGATGTG-3', exon 7, SEQ ID NO.:2) were synthesized, precipitated, and end labeled with $[\gamma^{32}P]ATP$ using T4 polynucleotide kinase. Probes were purified away from unincorporated nucleotides by gel filtration, and hybridized to plaques on nylon filters at 55° C. in 5×SSPE, 0.5 mg/ml heparin, 0.5% SDS for 3 hrs. Filters were washed 2× at room temperature in 5×SSPE, 0.1% SDS for 5 minutes, followed by a single 55° C. wash in the same solution. The filters were air dried and exposed to X-ray film. Positive plaques were cored from master plates, eluted in SM media, rescreened until single plaques were identified. Insert sizes were estimated using PCR on 0.4 µl of boiled phage stock using T3 and T7 sequencing primers (45° 1 min, 72° 3 min, 30 cycles). Inserts were excised as pBluescript SK plasmids via in vivo plasmid rescue (Ex-Assist kit, Stratagene). Inserts were sequenced with vector and internal primers using fluorescent dye terminators on an automated DNA sequencer. Sequence contigs, alignments, and analyses utilized Lasergene software for the Macintosh from DNASTAR.

EXAMPLE 2

RT-PCR of *C. elegans* RNA: Isolated cDNAs lacked sequences complementary to the NH2 terminus of known GAT1/NET family members as well as sequences matching inferred 5' exons of the T23G5.5 locus. An initial 5' end of the transporter's mRNA was amplified using reverse-transcriptase-mediated polymerase chain reactions (RT-PCR). Total *C. elegans* RNA was prepared with TRIZOL reagent (Sigma) according to manufacturer's recommendations and analyzed on 6% formaldehyde-agarose gels, according to Sambrook, J. et al., supra (1989). RNA was further treated with RQ1 RNase free Dnase prior to RT-PCR. RT-PCR was conducted with random priming of cDNA using oligonucleotides for PCR matching inferred exonic sequences. The first sense primer was located 5' of the hypothetical initiation codon of the T23G5.5 gene product (RB452: 5' CAAATCTTCAGACGATCCCGACGAA-3', SEQ ID NO:3). The antisense primer (RB453: 5' CTAGGATAATGAAAGTGGAAGACAC-3', SEQ ID NO:4) was designed from sequence of phage clone that, though not complete on its 5' end, extended past a presumptive translation termination codon and established a significant extent of the transporter's open reading frame (ORP), including novel 3' sequences (pCEGTλ1, FIG. 1). Using these primers, we amplified a single PCR product (pCeDAT1, FIG. 1) for ligation into the vector pGEMTEasy (Promega). Multiple clones bearing the cDNA insert were isolated and sequenced as described above. Missense mutations due to PCR in the 3' end of the cDNA were corrected by transfer of a nonmutant NcoI fragment from a nonmutant PCR isolate. A single missense mutation in the 3' end of the cDNA was corrected by oligonucleotide-mediated site-directed mutagenesis.

To obtain additional 5' cDNA sequences, a set of nested RT-PCR reactions using an SL1 primer (GCAGGATCCGGTTTAATTACCCAAGCTTGAG, SEQ ID NO:5), matching the 5' trans-spliced leader sequence found on the majority of C. elegans mRNAs (see, e.g., Conrad. R. et al., *RNA* 1, 164 (1995); Blaxter, M. et al. *Parasitology* 26(10), 1025 (1996), and two nested antisense primers (RB 515: 5'-AGTCCAGCTTTCCAG-ACCACTGTTC-3', SEQ ID NO:6 and RB516: 5' CTGGCCGAGGCACAACTCCATGTAG-3', SEQ ID NO:7), complementary to sequences in the 5' end of pCeDAT1, were used to identify the 5' end of CeDAT mRNA (FIG. 1). Following sequencing of this product to validate its T23G5.5 and CeDAT origin, this fragment was reamplified with a sense oligonucleotide complementary to sequences immediately adjacent to the SL1 primer. An SphI restriction site was added to the 5' end of this primer (RB5 17: 5'-GCGCGCATGCTCCATATTCCAAATTAGTCG-AAAAGCT-3', SEQ ID NO:8) to permit the use of an internal SphI site within the 5' RT-PCR product and pCeDAT1 to construct pCeDAT2 (FIG. 1). The completed pCeDAT2 5' end was sequenced to verify proper insertion and a lack of PCR-generated sequence errors.

EXAMPLE 3

Transient Expression of Transporters in HeLa cells: The vaccinia T7 expression system, according to Blakely, R. D. et al., *Anal. Biochem.* 194, 302 (1991), was used to determine whether isolated cDNAs encoded functional transporters in transfected cells. An aliquot of pCeDAT DNA was prepared using Qiagen DNA isolation columns and mixed with via lipofection in a 1:3 (g/vol) ratio at the time of transfection. HeLa cells were cultured in DMEM (10% fetal bovine serum, 100 μg/ml penicillin and 100 units/ml streptomycin) at 37° C. in 5%$CO_2$. One day before transfections, $1\times10^5$ cells were plated in 24 well tissue culture plates. Medium was removed and cells washed with sterile, phosphate-buffered saline (PBS). Vaccinia-virus suspensions were added in DMEM medium (50 μl) to cells and allowed to infect for 30 minutes at 37° C. followed by application of pCeDAT liposomes diluted in DMEM/0.45% BME (450 μl). Cells were assayed 6–12 hrs after transfections for induction of transport relative to plasmid vector or nontransfected cells. Transport assays were conducted at 37° C. in 500 μl final volume of KRH buffer (120 mM NaCl, 10 mM HEPES, 4.7 mM KCl, 1.2 mM $KH_2PO_4$, 1.2 mM $MgSO_4$, 2.2 mM $CaCl_2$, 10 mM D-glucose) containing 100 μM ascorbic acid, 100 μM paryglyine and 10 μM U-0251 (a known catecholamine O-methyl transferase inhibitor, Upjohn Laboratories). Assays were initiated by addition of radiolabeled substrates with or without varying concentrations of competitors. Amine transporter antagonists were preincubated with cells for 10 minutes prior to addition of substrate. Radiolabeled substrates examined included [$^3$H] DA, [$^3$H]NE, or [$^3$H]5HT. Ion-dependence of [$^3$H]DA transport was inspected in assays substituting $Li^+$ for $Na^+$ and isethionate for $Cl^-$ Assays were terminated by three ice cold washes in KRH prior to solubilization of cells and direct quantitation of accumulated radioactivity in a scintillation counter. Data were analyzed using Kaleidagraph software (Synergy Software), using a nonlinear least-squares curve fitting algorithm to fit concentration response curves and determine $IC_{50}$ values of competitors. $K_I$ values were estimated from $IC_{50}$ values using the Cheng-Prusoff correction for substrate concentration, according to Cheng, Y.-C. et al., *Biochem.Pharmacol.* 22, 3099 (1973).

EXAMPLE 4

Stable Expression of Transporters in GC4H1 Cells: The CeDAT insert was removed from pGMTE/CeDAT by digestion with restriction enzymes ApaI and NotI. The clone was then purified and ligated into pcDNA3.1(−) (InVitrogen). An aliquot of pcDNA3.1(−)/CeDAT was mixed with LipofectAMINE reagent (LifeTechnologies) in a 6:1 ratio at a final DNA concentration of 1 μg/ml in DMEM (serum/antibiotic free). GH4C1 (rat pituitary) cells, grown to about 10% confluence, were incubated in lipofectin:DNA for five hours at 37° C. The transfection medium was then removed and replaced by DMEM+10% FBS+penicillin and streptomycin. After an overnight incubation, the medium was removed and clones derived from single cells were selected by growing transfected cells at 37° C. with 5% CO2 in DMEM+FBS (dialyzed)+600 μg/ml G-418 (Life Technologies)+50 units/ml penicillin+5 μg/ml streptomycin.

To determine whether the transporter was stably expressed, transport assays were conducted at 37° C. in 0.5 KRH buffer (as detailed in Example 3) containing 0.1 mM ascorbate, 0.1 mM parygline and 26 nM [$^3$H] dopamine. For background incubations, 10 μM imipramine was added to block dopamine transport. 5 GC4H1/Ce5-HT cells were used as controls. Transport assays were terminated by rising cells with 0.5 ml of ice cold transport medium, and then solubilized in 3% SDS. Accumulated radioactivity was quantitated in a scintillation counter. All assay were done in triplicate.

EXAMPLE 5

Screening Assay for Transporter Inhibitors: GH4C1 cells transfected according to Example 4 were cultured in 48 well plates, under conditions outlined in Example 4. Mixtures of six random synthetic chemical compounds were added to each well, at a final concentration of 0.5 μM or 10 μM of each compound. Transport assays were then conducted according to the method described in Example 4. One sample reduced [$^3$H]dopamine transport to appropximately 50% of control levels. The six components of the sample were then rescreened, and a single compound was found to inhibit transport.

The references cited herein are incorporated by reference.

While various embodiments of the invention have been described above in detail, various modifications and adaptation thereof may be made without departing from the spirit and scope of invention as set forth in the claims below. Specifically, it is understood that those skilled in the art can modify specific cDNA sequences, for example by labeling, site-directed mutagenesis, substitution/deletion, or by fusion or insertion into an expression vector, without departing from the scope of the nucleotide and amino acid sequences of the present invention, nor methods of their use.

What is claimed is:

1. An isolated nucleic acid molecule encoding a nematode dopamine transporter, said transporter comprising the amino acid sequence set forth in SEQ ID NO:11.

2. An isolated nucleic acid molecule encoding the amino acid sequence of a nematode dopamine transporter protein expressed in nematodes, said nucleic acid comprising the nucleotide sequence as shown in SEQ. I.D. No.9, the nucleic acid being substantially free of nucleic acid that does not encode the amino acid sequence of SEQ I.D. No. 10.

3. The molecule of claim 1, comprising the nucleotide sequence of SEQ ID NO:9.

4. The molecule of any one of claims 1–3, further comprising a label for detection.

5. An expression vector comprising the DNA sequence of any one of claims 1–3, operatively linked to at least one control sequence compatible with a suitable host cell.

6. An expression system comprising an isolated host cell transformed with the expression vector of claim 5.

7. The expression system of claim 6 wherein the host cell is selected from the group consisting of prokaryotes, yeast and mammalian cells.

8. The expression system of claim 7 wherein the host cell comprises a HeLa cell.

9. The expression system of claim 7 wherein the host cell comprises MDCK cells, HEK-239 cells, or GH4C1 cells.

10. A process for producing a substantially purified nematode dopamine transport protein comprising:
   (a) culturing the transformed host cell of claim 6; and
   (b) purifying the protein form the cultured host cell.

11. The protein by the process of claim 10.

12. A method for identifying a dopamine transport antagonist, comprising;
   (A) providing a quantity of expression system of claim 6;
   (B) mixing said quantity with a sample of a compound to be measured; and
   (C) measuring inhibition of a dopamine uptake.

13. A method for identifying a dopamine transport stimulator, comprising the steps of:
   (A) providing a quantity of the expression system of claim 6;
   (B) mixing said quantity with a sample of a compound to be measured; and (C) measuring enhancement of dopamine uptake.

14. An isolated DNA probe consisting of the nucleic acid molecule of claim 1.

15. The DNA probe of claim 14 further comprising a label which enables detection of the probe.

16. A method for determining the presence of a nluicleic acid encoding a dopamine transporter in an organism suspected of carrying the nucleic acid, comprising:

(a) contacting the probe of claim 14 with a nucleic acid sample from the organism under suitable hybriding conditions; and (b) detecting the presence of the hybridized probe.

17. A purified dopamine transport protein comprising the sequence of amino acids as set forth in SEQ ID NO:11.

* * * * *